US010617502B2

(12) United States Patent
Nemeh et al.

(10) Patent No.: US 10,617,502 B2
(45) Date of Patent: Apr. 14, 2020

(54) CONCURRENT TREATMENT OF ORAL AND SYSTEMIC MALADIES USING DIRECT CURRENT ELECTRICITY

(71) Applicant: Biolectrics LLC, Cleveland, WI (US)

(72) Inventors: Issam Nemeh, Westlake, OH (US); William J. Leimkuehler, Jr., Rocky River, OH (US); James G. Azlein, Chagrin Falls, OH (US)

(*) Notice: Subject to any disclaimer, the term of this patent is extended or adjusted under 35 U.S.C. 154(b) by 199 days.

(21) Appl. No.: 15/882,101

(22) Filed: Jan. 29, 2018

(65) Prior Publication Data
US 2018/0161136 A1 Jun. 14, 2018

Related U.S. Application Data

(63) Continuation of application No. 15/583,194, filed on May 1, 2017, now Pat. No. 9,877,816, which is a (Continued)

(51) Int. Cl.
A61D 5/00 (2006.01)
A61N 1/32 (2006.01)
(Continued)

(52) U.S. Cl.
CPC .............. *A61D 5/00* (2013.01); *A61B 5/0534* (2013.01); *A61C 19/063* (2013.01);
(Continued)

(58) Field of Classification Search
CPC ...... A61D 5/00; A61B 5/0534; A61C 19/063; A61C 9/066; A61N 1/20; A61N 1/205;
(Continued)

(56) References Cited

U.S. PATENT DOCUMENTS 1,389,662 A 9/1921 Irwin
2,103,083 A 12/1937 Lynch
(Continued)

FOREIGN PATENT DOCUMENTS

EP 0599786 6/1994
EP 1525857 4/2005
(Continued)

OTHER PUBLICATIONS

Matsunaga, T. et al., Electrode System for the Determination of Microbial Populations, Applied and Environmental Microbiology, vol. 37 No. 1, Jan. 1979, p. 117-121.
(Continued)

*Primary Examiner* — Carl H Layno
*Assistant Examiner* — Erin M Piateski
(74) *Attorney, Agent, or Firm* — Smith Keane LLP

(57) ABSTRACT

A method and apparatus for the concurrent treatment of multiple oral diseases and defects while promoting general oral hygiene utilizing electricity are provided for non-human animals. Electrodes are used to deliver an electrical current to the gingival tissues of a mouth in order to achieve a number of therapeutic, prophylactic, and regenerative benefits. These benefits include killing oral microbes, increasing oral vasodilation, reducing oral biofilm, improving oral blood circulation, reversing oral bone resorption, promoting oral osteogenesis, treating gum recession, and fostering gingival regeneration. Other benefits include the treatment of gingivitis, periodontitis, and oral malodor, and other systemic diseases correlated with oral pathogens.

16 Claims, 9 Drawing Sheets

Related U.S. Application Data continuation of application No. 15/099,005, filed on Apr. 14, 2016, now Pat. No. 9,636,199, which is a continuation of application No. 14/102,171, filed on Dec. 10, 2013, now Pat. No. 9,314,321, which is a continuation-in-part of application No. 13/839,513, filed on Mar. 15, 2013, now Pat. No. 9,168,370, which is a continuation-in-part of application No. 12/205,062, filed on Sep. 5, 2008, now Pat. No. 8,660,669, which is a continuation-in-part of application No. 11/850,661, filed on Sep. 5, 2007, now abandoned.

(51) Int. Cl.
| | |
|---|---|
| A61N 1/30 | (2006.01) |
| A61N 1/20 | (2006.01) |
| A61N 1/05 | (2006.01) |
| A61C 19/06 | (2006.01) |
| A61B 5/023 | (2006.01) |
| A61B 5/053 | (2006.01) |

(52) U.S. Cl.
CPC .......... *A61C 19/066* (2013.01); *A61N 1/0548* (2013.01); *A61N 1/20* (2013.01); *A61N 1/205* (2013.01); *A61N 1/306* (2013.01); *A61N 1/32* (2013.01); *A61N 1/325* (2013.01)

(58) Field of Classification Search
CPC .......... A61N 1/306; A61N 1/32; A61N 1/325; A01K 15/026
USPC ...................................................... 607/134
See application file for complete search history.

(56) References Cited

U.S. PATENT DOCUMENTS

| | | |
|---|---|---|
| 2,151,738 A | 3/1939 | Buhse |
| D119,035 S | 2/1940 | Lindgren |
| 3,118,450 A | 1/1964 | Freeman et al. |
| 3,207,161 A | 9/1965 | Dietz |
| 3,215,139 A | 11/1965 | Dietz |
| 3,380,446 A | 4/1968 | Martin |
| 3,403,684 A | 10/1968 | Stiebel et al. |
| 3,502,076 A | 3/1970 | Bertolini |
| 4,153,060 A | 5/1979 | Korostoff et al. |
| 4,175,565 A | 11/1979 | Chiarenza et al. |
| D256,958 S | 9/1980 | Markham |
| 4,244,373 A | 1/1981 | Nachman |
| 4,378,007 A | 3/1983 | Kachadourian |
| 4,509,519 A | 4/1985 | Detsch |
| 4,802,444 A | 2/1989 | Markham et al. |
| D307,339 S | 4/1990 | Markham et al. |
| D308,122 S | 5/1990 | Markham et al. |
| 4,924,811 A | 5/1990 | Axelrod |
| 4,924,880 A | 5/1990 | O'Neill et al. |
| 5,034,847 A | 7/1991 | Brain |
| 5,131,383 A | 7/1992 | Juarez |
| 5,207,231 A | 5/1993 | Fakhri |
| RE34,352 E | 8/1993 | Markham et al. |
| 5,263,436 A | 11/1993 | Axelrod |
| D344,161 S | 2/1994 | Markham |
| D349,786 S | 8/1994 | Markham |
| 5,339,771 A | 8/1994 | Axelrod |
| 5,372,501 A | 12/1994 | Shalvi |
| 5,433,735 A | 7/1995 | Zanakis et al. |
| 5,490,520 A | 2/1996 | Schaefer et al. |
| D368,339 S | 3/1996 | O'Rourke et al. |
| 5,496,256 A | 3/1996 | Bock et al. |
| 5,725,377 A | 3/1998 | Lemler et al. |
| 5,741,500 A | 4/1998 | Yates |
| 5,792,067 A | 8/1998 | Karell |
| 5,832,877 A | 11/1998 | Markham |
| 5,857,431 A | 1/1999 | Peterson |
| 5,865,146 A | 2/1999 | Markham |
| D407,868 S | 3/1999 | Axelrod |
| 5,947,061 A | 9/1999 | Markham et al. |
| 6,067,941 A * | 5/2000 | Axelrod .............. A01K 15/026 119/707 |
| 6,212,435 B1 | 4/2001 | Lattner et al. |
| 6,212,535 B1 | 4/2001 | Weikart et al. |
| 6,254,391 B1 | 7/2001 | Darnell |
| 6,265,391 B1 | 7/2001 | Herbert |
| 6,405,681 B1 | 6/2002 | Ward |
| 6,415,740 B1 | 7/2002 | Curry |
| 6,439,166 B1 | 8/2002 | Markham |
| D462,487 S | 9/2002 | Axelrod |
| 6,546,896 B1 | 4/2003 | Markham |
| 6,615,766 B1 | 9/2003 | Curry |
| D504,748 S | 5/2005 | Jager |
| 7,044,737 B2 | 5/2006 | Fu |
| 7,087,260 B2 | 8/2006 | Axelrod |
| 7,111,587 B2 | 9/2006 | Rautenbach |
| 7,118,377 B2 | 10/2006 | Inoue et al. |
| 7,163,399 B2 | 1/2007 | Kajimoto et al. |
| D539,430 S | 3/2007 | Lowsky, Jr. et al. |
| RE39,563 E | 4/2007 | Markham |
| D544,655 S | 6/2007 | Hass |
| RE40,430 E | 7/2008 | Markham |
| D579,157 S | 10/2008 | Edwards |
| 7,640,894 B2 | 1/2010 | Jager |
| 7,775,795 B2 | 8/2010 | Khawaled et al. |
| D626,706 S | 11/2010 | Ragonetti |
| 7,874,294 B2 | 1/2011 | Burger |
| 7,886,398 B2 | 2/2011 | Morita et al. |
| 7,917,223 B2 | 3/2011 | Madjar et al. |
| D638,589 S | 5/2011 | Axelrod et al. |
| 8,060,220 B2 | 11/2011 | Liebergesell et al. |
| D658,825 S | 5/2012 | Wolfe, Jr. et al. |
| 8,225,747 B2 | 7/2012 | Markham et al. |
| 8,276,547 B2 | 10/2012 | Markham |
| D677,439 S | 3/2013 | Renforth |
| 8,393,300 B2 | 3/2013 | Markham et al. |
| 8,479,750 B2 | 7/2013 | Schaefer et al. |
| D688,836 S | 8/2013 | Costello |
| D689,155 S | 9/2013 | Jahns |
| 8,660,669 B2 | 2/2014 | Nemeh |
| 2001/0012608 A1 | 8/2001 | Darnell |
| 2003/0079693 A1 | 5/2003 | Jager |
| 2004/0137118 A1 | 7/2004 | Axelrod |
| 2004/0186418 A1 | 9/2004 | Karashima |
| 2005/0037311 A1 | 2/2005 | Bergersen |
| 2005/0203587 A1 | 9/2005 | Liebergesell |
| 2006/0178703 A1 | 8/2006 | Huston et al. |
| 2006/0201446 A1 | 9/2006 | Edwards |
| 2006/0271148 A1 | 11/2006 | Liebergesell et al. |
| 2007/0203389 A1 | 8/2007 | Bergman |
| 2007/0224572 A1 | 9/2007 | Jon |
| 2007/0224898 A1 | 9/2007 | DeAngelis et al. |
| 2007/0259316 A1 | 11/2007 | Conrad et al. |
| 2008/0003540 A1 | 1/2008 | Khawaled et al. |
| 2008/0233541 A1 | 9/2008 | De Vreese et al. |
| 2008/0280248 A1 | 11/2008 | Pitts et al. |
| 2008/0314333 A1 | 12/2008 | Hurwitz |
| 2009/0117513 A1 | 5/2009 | Nemeh et al. |
| 2010/0224138 A1 | 9/2010 | Axelrod et al. |
| 2011/0039226 A1 | 2/2011 | Armanino |
| 2011/0117515 A1 | 5/2011 | Jablow |
| 2011/0179851 A1 | 7/2011 | MacK et al. |
| 2011/0289707 A1 | 12/2011 | Schaefer et al. |
| 2012/0156648 A1 | 6/2012 | Kaufman et al. |
| 2012/0256750 A1 | 10/2012 | Novak |
| 2012/0272922 A1 | 11/2012 | Axelrod et al. |
| 2013/0072851 A1 | 3/2013 | Doll et al. |
| 2013/0209964 A1 * | 8/2013 | Nemeh ................ A61C 19/063 433/216 |

FOREIGN PATENT DOCUMENTS

| | | |
|---|---|---|
| WO | 1979/001082 | 12/1979 |
| WO | 1992/005753 | 4/1992 |

(56) References Cited

FOREIGN PATENT DOCUMENTS

| | | |
|---|---|---|
| WO | 2005/062710 | 7/2005 |
| WO | 2006/018525 | 2/2006 |

OTHER PUBLICATIONS

Caubet, R., et al., A Radio Frequency Electric Current Enhances Antibiotic Efficacy . . . , Antimicrobial Agents and Chemotherapy, vol. 48, No. 12, Dec. 2004, pp. 4662-4664.
Giladi, M., et al., Microbial Growth Inhibition by Alternating Electric Fields, Antimicrobial Agents and Chemotherapy, vol. 52, No. 10, Oct. 2008, pp. 3517-3522.
Del Pozo, J.L., et al., The Electricidal Effect is Active in an Experimental Model . . . , Antimicrobial Agents and Chemotherapy, vol. 53, No. 10, Oct. 2009, pp. 4064-4068.
Del Pozo, J.L., et al., Effect of Electrical Current on the Activities of Antimicrobial Agents . . . Antimicrobial Agents and Chemotherapy, vol. 53, No. 1, Jan. 2009, pp. 35-40.
Del Pozo, J.L., et al., The Electricidal Effect: Reduction of *Staphylococcus* . . . , Antimicrobial Agents and Chemotherapy, vol. 53, No. 1, Jan. 2009, pp. 41-45.
Davidovitch, Z., et. al., Effect of electric currents on gingival cyclic nucleotides in vivo (Abstract). Journal of Periodontal Research, 1980, 15: 353-362.
Hashimoto, H., Effect of micro-pulsed electricity on experimental tooth movement (Abstract). Nihon Kyosei Shika Gakkai Zasshi, Aug. 1990, 49(4):352-61.
Horning, GM., et al., The prevalence of periodontitis in a military treatment problem (Abstract). J Am Dent Assoc., Nov. 1990, 121(5):616-22.
Onkormanyzat, F., et al., The use of iontophoresis in dental practice (Abstract). Fogorv Sz. Jun. 1993, 86(6):205-12.
Wang, Q., et al., Osteogenesis of electrically stimulated bone cells mediated in part by calcium ions (Abstract), Clin Orthop Relat Res. Mar. 1998, (348):259-68.
Davidovitch, Z, et al., Electric currents, bone remodeling, and orthodontic tooth movement. II. Increase in rate of tooth . . . (Abstract), Am J Orthod, Jan. 1980, 77(1):33-47.
Buch, F., et al., Direct current influence on bone formation in titanium implants (Abstract). Biomaterials, Nov. 1984, 5(6):341-6.
Puhar, I., et al., Efficacy of electrical neuromuscular stimulation in the treatment of chronic periodontitis. J Periondontal Implant Sci 2011; 41:117-122.
Bolton, L., et al., Direct-Current Bactericidal Effect on Intact Skin. Antimicrobial Agents and Chemotherapy, Jul. 1980, vol. 18, No. 1, pp. 137-141.
Ehrlich, G.D., et al., Engineering Approaches for the Detection and Control of Orthopaedic Biofilm Infections, Clin Orthop Relat Res. Aug. 2005, (437):59-66.
Matl, FD., et al., Augmentation of antibiotic activity by low-frequency electric . . . (Abstract). Bioelectromagnetics, Jul. 2011, 32(5):367-77.
Sandhu, SP., et al., Comparative evaluation of different strengths of electrical current . . . (Abstract). Indian J Dent Res. Apr.-Jun. 2010; 21(2):207-12.
Kaynak, D., et al., A histopathologic investigation on the effects of electrical stimulation . . . (Abstract). J Periodontol, Dec. 2005, 76(12):2194-204.
Hagiwara, T., et al., Effect of electrical stimulation on mandibular distraction osteogenesis (Abstract). J Craniomaxillofac Surg, Feb. 2000, 28(1):12-9.
Chakkalakal, DA., et al., Electrophysiology of direct current stimulation of fracture . . . (Abstract). IEEE Trans Biomed Eng., Nov. 1990, 37(11):1048-58.

Kane, WJ. Direct current electrical bone growth stimulation for spinal fusion (Abstract). Spine (Phila Pa 1976), Mar. 1988, 13(3):363-5.
Periodontal Disease Fact Sheet, American Academy of Periodontology, www.perio.org/newsroom/periodontal-disease-fact-sheet, Oct. 10, 2013.
Manuelderegil@xxxxxxxxx. "Perioprotect ripoff", perioprotect. ripoff, Mar. 20, 2009.
Petersen, P.E., et al., Strengthening the prevention of periodontal disease: the WHO approach, J Periodontol, Dec. 2005, vol. 76, No. 12, pp. 2187-2193.
Pitman, S., US Army develops tooth-cleaning gum, Cosmetics design.com, Dec. 21, 2005.
Bloomberg Businessweek, Why P&G's Smile is So Bright, Jul. 31, 2002, 4 pages.
Hitti, M., 9 Risk Factors for Tooth Loss, WebMD.com, Nov. 11, 2005, 3 pages.
American Dental Association, Key Dental Facts, Sep. 2008, 26 pages.
Karolefski, J., Changing Habits. Supermarket News., Feb. 16, 2009, http://supermarketnews.com/print/nonfood/changing-habits, 4 pages.
Dental Managment:Cost of Deep Perio Cleaning from a Dentist . . . Oct. 10, 2013, http://thewealthydentist.com/SurveyResults/119-Perio-Cleaning.htm, 2 pages.
Johnsen, M., 2009 Hot Products: Editor's Picks. Drug Store News, Jun. 2009, www.drugstorenews.com, 17 pages.
Ichimura, K., et al., Effect of weak electric current on reducing oral bacteria in vitro. Bull. Tokyo dent. Coll., vol. 42, No. 2, pp. 97-100, May 2001.
Poortinga, A.T., et al., Electric field induced desorption of bacteria from a conditioning film covered substratum. Biotechnology and Bioengineering, vol. 76(4):395-99 Dec. 2001.
Glazer, P.A., et al., Electricity: The history and science of bone growth stimulation for spinal fusion. The Orthopaedic Journal at Harvard Medical School, 2002, pp. 63-67.
Albandar, J.M., et al., Gingival recession, gingival bleeding, and dental calculus in adults 30 years of age and older . . . J Periodontol, Jan. 1999, vol. 70, No. 1, pp. 30-43.
Banga, A.K., et al., Iontophoresis and electroporation: comparisons and contrasts. International Journal of Pharmaceutics 179 (1999) pp. 1-19.
Piekarski, K., et al., Osteogenetic stimulation by externally applied DC current. Acta Orthop. Scand. vol. 49, pp. 113-120, 1978.
Hartshorne, E. On the causes and treatment of pseudarthrosis and especially that form of it sometimes called supernumerary joint. Am J Med, Jan. 1841; vol. 1; pp. 121-156.
Tronstad et al., "Effect of Electric Current and Silver Electrodes on Oral Bacteria", Endod Dent Traumatol 1985; 1:112-115.
Guthmiller et al., Chapter 8—Peridontal Diseases (pp. 1-19), Polymicrobial Disease, (Washington (DC); ASM Press; 2002).
Gaitte-Jardim Junior et al, "Microbiota Associated with Chronic Osteomyelitis of the Jaw," Brazilian Journal of Microbiology, vol. 41, No. 4, Sao Paulo, Oct. /Dec. 2010.
Han et al., "Term Stillbirth Caused by Oral Fusobacterium nucleatum," Obstetrical Gynecology, 2010, 115: 442-5.
Hintao et al., "The Microbiological Profiled of Saliva, Supragingival and Subgingival Plaque and Dental Caries in Adults with and without Type 2 Diabetes Mellitus," Oral Microbiology Immunology, 2007: 22: 175-181.
USPTO Office Action dated May 13, 2016 regarding U.S. Appl. No. 15/099,005, 13 pages.
USPTO Office Action dated Oct. 6, 2016 regarding U.S. Appl. No. 15/099,005, 10 pages.
USPTO Office Action dated May 24, 2017 regarding U.S. Appl. No. 15/583,194, 7 pages.

* cited by examiner

CONCURRENT TREATMENT OF ORAL AND SYSTEMIC MALADIES USING DIRECT CURRENT ELECTRICITY

RELATED APPLICATIONS

This application is a continuation of U.S. patent application Ser. No. 15/583,194, filed May 1, 2017, now U.S. Pat. No. 9,877,816 and entitled "Concurrent Treatment of Oral and Systemic Maladies in Animals Using Electrical Current," which is a continuation of U.S. patent application Ser. No. 15/099,055, filed Apr. 14, 2016, now U.S. Pat. No. 9,636,199, and entitled, "Concurrent Treatment of Oral And Systemic Maladies In Animals Using Electrical Current," which is a continuation of U.S. patent application Ser. No. 14/102,171, filed Dec. 10, 2013, now U.S. Pat. No. 9,314,321, and entitled "Concurrent Treatment Of Oral And Systemic Maladies In Animals Using Electrical Current," which is a continuation-in-part of U.S. patent application Ser. No. 13/839,513, filed Mar. 15, 2013, now U.S. Pat. No. 9,168,370, and entitled "Concurrent Treatment Of Oral And Systemic Maladies Using Direct Current Electricity," which is a continuation-in-part of U.S. patent application Ser. No. 12/205,062 filed Sep. 5, 2008, now U.S. Pat. No. 8,660,669, and entitled "Concurrent Treatment of Oral Maladies Using Direct Current Electricity," which is a continuation-in-part of U.S. Ser. No. 11/850,661 filed on Sep. 5, 2007, now abandoned, and entitled "Hygiene Mouthpiece," all of which are incorporated by reference herein in their entireties.

BACKGROUND

This invention relates to an apparatus configured to concurrently promote general oral hygiene, treat periodontal diseases such as gingivitis and periodontitis, kill oral microbes including cavity-causing bacteria, reduce oral biofilms, increase blood flow in oral tissues, increase salivation, promote gingival tissue regeneration, foster osteogenesis in the boney structures of the teeth, mouth and related areas, treating systemic diseases associated with oral bacteria, and treat other periodontal and oral maladies through the non-invasive application of weak direct current electricity to the surfaces in the oral cavity, and it also relates to an apparatus suitable for providing direct current electricity for these therapeutic, prophylactic, and regenerative effects.

Periodontal disease has been identified as a risk factor for various systemic diseases by both dentists and physicians. Included in these diseases are cardiovascular disease, adverse pregnancy outcomes, and diabetes with newfound evidence supporting its association with pancreatic diseases and arthritis. While many of the studies establish correlation between the presence of periodontal disease and these systemic conditions, causation, with most of these conditions, is still a subject of ongoing research. A few of the biological mechanisms which have been proposed as to how oral bacteria stemming from periodontal disease can cause systemic disease are as followed:

1. Direct Effect of Oral Infections:

Oral microbes and their byproducts can gain systemic access via the circulatory system through traveling through compromised tissue and inflamed periodontium in the oral cavity. In gaining systemic access, oral microbes have the potential to directly influence subclinical mediators of various systemic diseases.

2. Inflammation:

People with periodontal disease have elevated levels of systemic inflammatory markers due to the burden of increased levels of oral bacteria. Treatment for periodontal disease has been reported to decrease systemic inflammation levels.

3. Cross-Reactivity:

The progression of systemic diseases can be accelerated by the immune response to bacterial heat-shock proteins creating antibodies that cross-react with innate heat shock proteins expressed on cells of the damaged tissues.

Cardiovascular Disease

Studies investigating the potential association between periodontal disease and cardiovascular diseases, including atherosclerosis, coronary heart disease, and stroke have found a significant positive correlation between poor oral health and the prevalence of cardiovascular disease. While both diseases share several common risk factors, recent studies suggest that periodontitis may precede and therefore contribute to atherosclerotic complications. In fact, meta-analyses show that subjects suffering from periodontitis experience an increased risk for developing cardiovascular diseases.

While it has not been definitively shown if these bacteria initiate atherosclerosis or rather invade an already compromised artery, antibodies to periodontal bacteria, including *Fuseobacterium nucleatum* and *Streptococcus oralis*, have been found in blood serum and are associated with an increased risk of coronary heart disease. A mouse study found that intravenous inoculation with *Porphyromonas gingivalis* accelerated atherosclerotic development. Further, following oral inoculation, *P. gingivalis* DNA was found in the aortic tissue of those infected mice that showed observable signs of accelerated early atherosclerosis. Another study has named *F. nucleatum* as a synergistic agent with *P. gingivalis*. *F. nucleatum* enhances the ability of *P. gingivalis* to invade host cells due to a coaggregating effect between the two organisms. This is significant as bacteria within the atheroma may lead to the development of atherosclerotic plaque. The evidence thus far supports the idea that periodontitis leads to systemic exposure to oral bacteria which serves as a potential source of systemic inflammatory mediators, cytokines produced in the infected periodontal tissues, capable of initiating or worsening atherosclerosis and coronary heart disease when they enter into the blood stream. Clinical studies on periodontal disease have also revealed a positive association with coronary disease and emphasis is now being placed on understanding the exact relation between periodontal disease and atherosclerosis.

Pre-Term Birth

*Fusobaceterium nucleatum*, one of the most prevalent species of bacteria found in amniotic fluid and placental infections that cause preterm birth, is also often named the sole infectious agent in preterm labor with intact fetal membranes. *F. nucleatum* is also highly associated with various types of periodontal disease. During periodontal infection, when the oral mucosa is injured and inflamed and the quantities of periodontal pathogens increase dramatically, transient levels of bacteria can appear in the blood leading to selective colonization of undesired sites. One study demonstrated that pregnant mice injected hematogenously with *F. nucleatum* isolated from either amniotic fluid infection or an oral source resulted in fetal death.

Recently, a human stillbirth case was analyzed and it was found that the *F. nucleatum* did indeed originate from the mother's oral cavity, a fact that had not yet been proven. It is likely that the *F. nucleatum* translocated from the mother's mouth via the blood stream where it was then able to cross the endothelium to proliferate and colonize within the fetal membranes, amniotic fluid and fetus whereupon its presence lead to fetal demise. In a mouse model, hematogenous injection of *F. nucleatum* into pregnant mice resulted in specific bacterial colonization in the placenta causing localized inflammation. *F. nucleatum* was completely cleared from the maternal circulation after 24 hours of injection. However, once colonized in the immune privileged placenta, the bacteria proliferated quickly and caused fetal death within 3 days. Chronic periodontal disease could mediate infection through the translocation of periodontal bacteria/inflammatory markers to the fetoplacental unit.

Diabetes

Diabetes mellitus is an endocrine disease that stems from genetic, environmental and behavioral risk factors. For the past several decades, diabetes has been considered a modifying factor for periodontal disease with recent years suggesting a bidirectional relationship between the two. Further, presence of periodontal disease has been implicated as a risk for diabetic complications, namely poor glycemic control. Recent longitudinal and systemic studies have seen periodontal disease correlated to higher risks of death from ischemic heart disease, diabetic nephropathy, end-stage renal disease and increased insulin resistance compared to patients with mild or no periodontal disease. In type II diabetes, insulin resistance is linked to the actions of pro-inflammatory cytokines. It is believed that periodontal disease leads to a significantly higher amount of these serum markers of inflammation, thus conferring insulin resistance. A human study examining the bacterial content of adults with and without type II diabetes found diabetic patients had significantly more severe periodontitis and higher levels of many oral bacteria, including *Streptococcus oralis*.

Pyogenic Liver Abscess

*F. nucleatum* has recently been implicated in pyogenic liver abscess (PLA). Normally caused by biliary tract pathology, diverticular disease and bowel malignancy, atrophic gastritis and cryptogenic liver disease, PLA caused by *F. nucleatum* is very rare with *Escherichia coli*, *Klebsiella* and *Enterobacter* being the most commonly isolated microorganisms in the drained abscesses. *F. nucleatum* was found in the liver abscess with no other infectious source being found, except for a dental extraction. It is hypothesized that due to the coaggregation properties of *F. nucleatum*, it is able to transport and breach the mucosa of the colon and lead to bacteremia which results in hepatic abscess.

Osteomyelitis

Osteomyelitis is a bone infection caused by bacteria, fungi or other germs. Commonly, bacteria spreads to the bone from infected skin, muscles or tendons and often time occur under a skin sore. The infection can also start in another part of the body and spread hematogenously. Occasionally *Fusobacterium* species have been isolated from bone/joint infections in the head and neck area and were associated with chronic periodontitis. A recent study has reported a case of osteomyelitis caused by *F. nucleatum* in conjunction with muscle abscess. The patient had no known predisposing factors and had no other infection sources except a history of periodontal disease. It is believed that due to the patient's poor oral hygiene, *F. nucleatum* bacteremia may have developed and lead to a hematogenous osteomyelitis of the lower leg.

Arthritis

Numerous clinical studies have suggested a potential association between rheumatoid arthritis (RA) and periodontal disease as several oral bacteria species, such as *P. gingivalis* and *Prevotella intermedia*, have been isolated from the synovial fluid of patients. Periodontal disease is thought to allow bacteria to penetrate through the permeable pocket epithelial in the oral cavity to reach the underlying gingival connection tissue. From there, it may be transported out into the bloodstream with the ability to colonize elsewhere within the body. The oral bacteria found in the synovial fluid of patients suffering from RA has been attributed to synovial inflammation favorably trapping oral bacteria DNA, which suggests periodontal disease may have a perpetuating effect on joint diseases. Therefore, periodontitis may in fact be a factor leading to the autoimmune inflammatory responses characteristic of RA. Patients suffering from RA may also be at a higher risk of developing periodontal disease thus suggesting a bidirectional relationship between the two conditions. One particular study examined the presence of bacterial DNA in the synovial fluids of native and failed prosthetic joints of patients suffering from arthritis. Out of the 5 patients where bacterial DNA was found, *F. nucleatum* was detected in 4 of these 5 patients. This suggests that this bacterium can translocate from the oral cavity to the synovial fluid, as *F. nucleatum* was also found in the patient's plaque sample.

Oral Biofilm

Periodontitis, gingivitis, and caries are infectious diseases of the oral cavity in which oral biofilm plays a causative role. Biofilm formation is also involved in the pathogenesis of dental implant failures such as peri-implantitis, denture stomatitis, and oral yeast infections such as candidiasis. Oral biofilms begin with dental pellicle formation on the teeth. This pellicle is composed of salivary proteins that coat the exposed surfaces of the teeth, primarily the supra-gingival ones, to which the planktonic bacteria begin to adhere. The aerobic bacteria, including gram-positive cocci, such as *S. oralis*, are the early colonizers that begin forming the initial biofilm colony, primarily through cellular division of the adherent bacteria.

Once the initial colony has been established, other co-aggregating bacteria species, such as *F. nucleatum, P. gingivalis*, and other gram-negative, anaerobic bacteria attach to the previously formed colonies. As these colonies mature, they grow to cover the sub-gingival surfaces of the teeth and begin to induce inflammation in the periodontium.

SUMMARY OF THE INVENTION

The present invention relates to an apparatus for aiding overall oral health of a non-human animal, and more particularly to treating periodontal diseases such as gingivitis and periodontitis, killing oral microbes including cavity-causing bacteria, reducing oral biofilms, increasing blood flow in oral tissues, increasing salivation, promoting gingival tissue regeneration, fostering osteogenesis in the boney structures of the teeth, mouth and related areas, treating systemic diseases associated with oral bacteria, and treating other periodontal and oral maladies through the non-invasive application of weak direct current electricity to the surfaces in the oral cavity.

One aspect of the present invention is to provide an apparatus for promoting oral hygiene in a non-human animal comprising a body sized and configured to be received in the non-human animal mouth, the body extending along a longitudinal length between and including a first end and an opposite second end and defining a cavity therewithin; a cathodic electrode supported by the body; a anodic electrode supported by the body spaced from the cathodic electrode, wherein the plurality of cathodic electrodes and the plurality of anodic electrodes are disposed in alternating fashion circumferentially about the body; and having a power supply housed within the cavity and being electrically connected to the plurality of cathodic electrodes and the plurality of anodic electrodes.

The apparatus may further include a first conductive material portion secured over the plurality of cathodic electrodes.

The apparatus may further include a second conductive material portion secured over the plurality of anodic electrodes.

The apparatus may further include an insulative portion disposed at least partially between the first conductive material portion and the second conductive material portion.

Additionally or alternatively the apparatus may have a configuration wherein the plurality of cathodic electrodes and the plurality of anodic electrodes are centered along the longitudinal length of the body between the first end and the second end.

Additionally or alternatively the body may have a substantially geometric stadium cross-section at its longitudinal mid-point, the cross-section having two opposite substantially straight sides connected by two opposite substantially curved ends.

The apparatus may further have a third cathodic electrode and a third anodic electrode, wherein each straight side comprises one of the plurality of cathodic electrodes and one of the plurality of anodic electrodes, and wherein one of the two curved ends comprises one of the plurality of cathodic electrodes and the other of the two curved ends comprises one of the plurality of anodic electrodes.

Additionally or alternatively the conductive material portions extend radially outward beyond the insulative portion.

Additionally or alternatively the conductive material portions comprise a resilient material having a hardness value on the Shore A durometer hardness scale.

The conductive material portions may have a Shore A hardness value of 25-80 on the Shore A durometer hardness scale.

The insulative portion may comprise a resilient material of approximately the same hardness as the conductive material portion.

The insulative portion may comprise a resilient material having a hardness approximately half the hardness of the conductive material portions.

Another aspect of the invention is to provide an apparatus for promoting oral hygiene in a non-human animal comprising: including a body sized and configured to be received in the non-human animal mouth, the body extending along a longitudinal length between and including a first end and an opposite second end and defining a cavity therewithin; a cathodic electrode supported by the body; a anodic electrode supported by the body; a power supply housed within the cavity and being electrically connected to the cathodic electrode and the anodic electrode: and a control board, comprising a timer, housed within the cavity configured to facilitate the transfer of the power of the power supply to the cathodic electrode and the anodic electrode, wherein the timer is configured to deactivate the electrodes at a predetermined time after activation.

The apparatus may also have a first conductive material portion secured over the cathodic electrode.

The apparatus may also have second conductive material portion secured over the anodic electrode.

The apparatus may also have an insulative portion disposed at least partially between the first conductive material portion and the second conductive material portion;

Another aspect of the invention is to provide an apparatus for promoting oral hygiene in a non-human animal which has a body sized and configured to be received in the non-human animal mouth, the body extending along a longitudinal length between and including a first end and an opposite second end and defining a cavity therewithin; a cathodic electrode supported by the body; a anodic electrode supported by the body spaced from the cathodic electrode; a power supply housed within the cavity and being electrically connected to the cathodic electrode and the anodic electrode: and an on/off switch configured to control whether power supply power is available for delivery to the electrodes.

The apparatus may also have a first conductive material portion secured over the cathodic electrode;

The apparatus may also have a second conductive material portion secured over the anodic electrode;

The apparatus may also have an insulative portion disposed at least partially between the first conductive material portion and the second conductive material portion;

DETAILED DESCRIPTION

Figure 1:
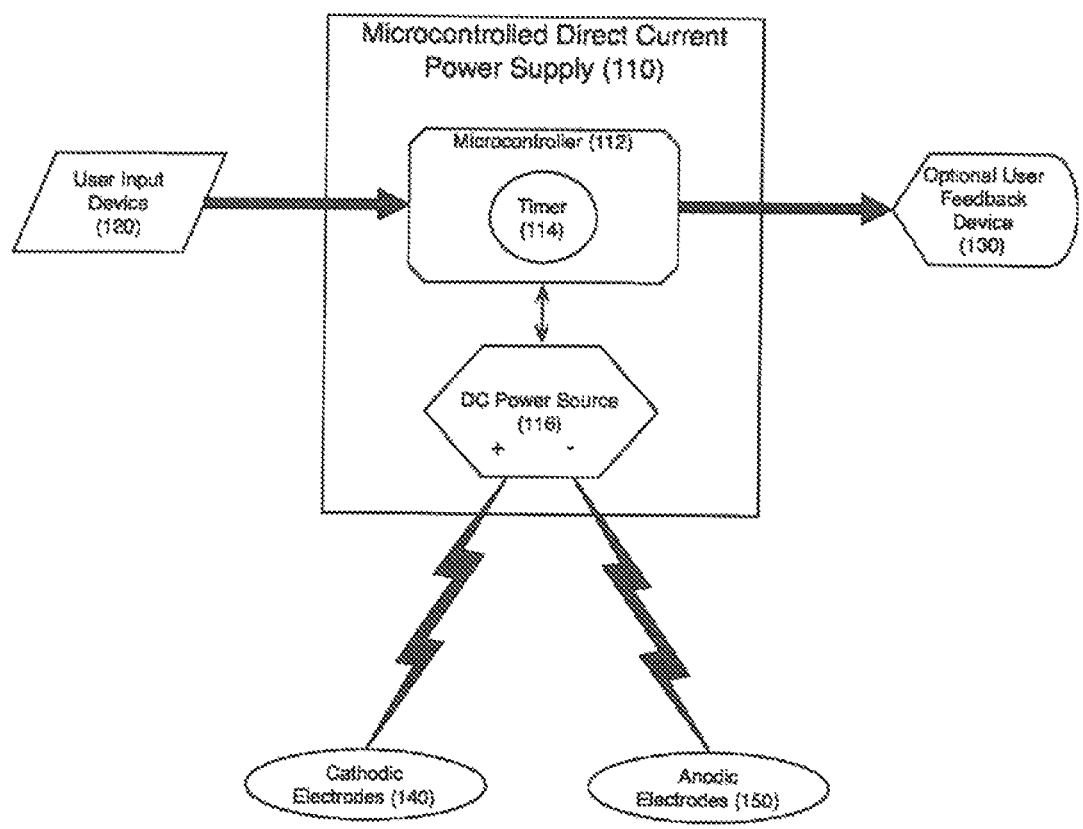
FIG. 1 demonstrates the overall structure of the first embodiment of a device according to the present invention, including a microcontrolled power source, user input, user feedback and oral electrodes.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is known in the art that oral bacteria cannot survive when exposed to low-microampere direct current electricity. This method of killing oral bacteria and treating bacteria-caused conditions such as gingivitis has been demonstrated in Nachman, U.S. Pat. No. 4,244,373 of Jan. 13, 1981 and in Detsch, U.S. Pat. No. 4,509,519 of Apr. 9, 1985. Killing oral bacteria has the added benefit of preventing tooth decay and dental caries, or cavities. Generally, tooth decay is attributed to aerobic acid-producing bacteria whose acid causes uncompensated demineralization of the teeth. However, Nachman does not instruct optimal approaches to reducing oral bacteria including aerobic and anaerobic bacteria on a species-by-species level and instead teaches a generic, untargeted treatment.

While researching the effect of direct current electricity on the mouth, the applicants discovered that by increasing the current level to the approximate range of 50 to 250 microamperes, a direct current electrical treatment was able to deliver new and unexpected therapeutic, prophylactic, and regenerative benefits previously unknown in the art.

Specifically, by utilizing a direct current in the aforementioned range, not only did such a treatment kill bacteria, but it was also found to kill or disable viruses and fungus as well. Studies from the podiatric field have shown that higher current levels than those used in existing oral electrical treatments are necessary to effectively treat fungal infections ("Low-Voltage Direct Current as a Fungicidal Agent for Treating Onychomycosis", Kalinowski, et al., Journal of the American Podiatric Medical Association Vol. 94 No. 6: 565-572, 2004). By applying this knowledge of increased current levels from research outside the art, the applicants were able to add fungicidal and viricidal benefits to a method already known to be bactericidal. The applicants' studies have shown that these microbicidal properties begin to take effect within approximately 5 and 15 minutes of treatment, reducing both supra- and sub-gingival microbes.

In addition, the applicants' clinical research unexpectedly demonstrated that a direct current in the approximate range of 50 to 250 microamperes was able to regenerate gingival tissues, providing a non-surgical treatment alternative for those with recessed gums. While the osteogenic properties of electricity have been known in the art, the connection between nonosseous tissue regeneration and electricity were not well known in the art prior to these experiments. The unique current range associated with the method and apparatus of this invention is one of a few effective methods in the dental field to accomplish effective gingival tissue regeneration in a non-surgical manner.

In further research, the applicants conducted preclinical testing that examined the effects of direct current stimulation on three different oral bacteria (*F. nucleatum, S. oralis, P. gingivalis*) in both saline and saliva solutions. This testing varied the current levels, inoculum size of bacteria, solution medium, and treatment time to develop an optimal treatment to reduce these three bacteria species associated with both periodontal and systemic diseases.

The results of this testing yielded unexpected results and showed that each different bacterium had a different dose response to DC stimulation. Through this testing, the applicants identified treatment parameters that were able to kill up to 100% of *S. oralis*, 99.1% of *F. nucleatum*, and 52.3% of *P. gingivalis* in a single treatment lasting thirty minutes or less. This research yielded specifications for DC-based treatments of targeted pathogens that was previously unknown in the art. The optimal treatment parameters discovered in this research and described in this method can provide an innovative way to reduce these three species of bacteria, in both supra- and sub-gingival environments, and thus prevent and/or treat their associated complications including periodontal disease, biofilm formation, as well as the systemic diseases correlated to these oral pathogens.

In addition, scanning electron microscopy (SEM) was conducted on *F. nucleatum* colonies before and after at 30 minute treatment, according to the method of this invention, to better understand the mechanism by which the method according to this invention is able to reduce bacterial levels. The SEM imagery suggested that the method according to this invention interferes with bacterial cellular division and can weaken the outer envelope (cell membrane) resulting in fragile cellular structures that can easily break. It is contemplated that this is phenomenon is an example of electroporation, where the permeability of cellular membranes may be affected by electrical stimulation either temporarily or permanently. It is further contemplated that the electroporation caused by the method according to this invention could play a role in developing new therapies in molecular biology which would take advantage of this cellular permeability and introduce new material into the cells of oral pathogens or oral tissues through mechanisms including, but not limited to genetic material (transfection) such as DNA, RNA, sRNA, siRNA, plasmids, etc. These effects would prove a new tool in targeted gene therapies for oral applications.

Specifically, the method according to the present invention has been shown to reduce viable colony forming units (CFU) in various oral bacteria.

Table 1 below shows the efficacy of treatment according to the present invention at current levels of 50 µA or 500 µA for 5, 10, 20 and 30 minute durations for bacterial cultures ranging from $10^4$ to $10^7$ colony forming units (CFU) of *Streptococcus oralis* in a saline solution.

TABLE 1

In Vitro Efficacy of Device Against *Streptococcus oralis* in Saline

| CFU | µA | 0 Min | 5 Min | 10 Min | 20 Min | 30 Min |
|---|---|---|---|---|---|---|
| 10e4 | 50 µA | 1120 | 1080 | 600 | 320 | 280 |
|  | 500 µA | 1120 | 1200 | 800 | 240 | 0 |
| 10e5 | 50 µA | 10000 | 9600 | 8400 | 9200 | 7600 |
|  | 500 µA | 11600 | 10400 | 11200 | 10800 | 8400 |
| 10e6 | 50 µA | 80000 | 63200 | 52800 | 32400 | 24800 |
|  | 500 µA | 80800 | 70000 | 15200 | 14000 | 15600 |
| 10e7 | 50 µA | 1280000 | 1080000 | 1040000 | 800000 | 440000 |
|  | 500 µA | 1080000 | 520000 | 160000 | 120000 | 320000 |

Table 2 below shows the efficacy of treatment to the present invention at current levels of 50 µA or 500 µA for 5, 10, 20 and 30 minute durations for bacterial cultures ranging from $10^4$ to $10^7$ CFU of *Streptococcus oralis* in a saliva solution.

TABLE 2

In Vitro Efficacy of Device Against Streptococcus oralis in Saliva

| CFU | μA | 0 Min | 5 Min | 10 Min | 20 Min | 30 Min |
|---|---|---|---|---|---|---|
| 10e4 | 50 μA | 160 | 160 | 80 | 80 | 40 |
|  | 500 μA | 200 | 80 | 80 | 80 | 80 |
| 10e5 | 50 μA | 5600 | 5600 | 6800 | 5600 | 4000 |
|  | 500 μA | 8400 | 6800 | 7200 | 6400 | 2800 |
| 10e6 | 50 μA | 25600 | 25200 | 15200 | 17200 | 18400 |
|  | 500 μA | 23600 | 16800 | 15600 | 17600 | 15200 |
| 10e7 | 50 μA | 316000 | 284000 | 300000 | 276000 | 220000 |
|  | 500 μA | 324000 | 328000 | 300000 | 292000 | 252000 |

Table 3 below shows the efficacy of treatment to the present invention at current levels of 50 μA or 500 μA for 5, 10, 20 and 30 minute durations for bacterial cultures ranging for $10^4$ and $10^6$ CFU of *Fusobacterium nucleatum* in a saline solution.

TABLE 3

In Vitro Efficacy of Device Against Fusobacterium nucleatum in Saline

| CFU | μA | 0 Min | 5 Min | 10 Min | 20 Min | 30 Min |
|---|---|---|---|---|---|---|
| 10e4 | 50 μA | 480 | 280 | 280 | 120 | 40 |
|  | 500 μA | 560 | 440 | 400 | 200 | 120 |
| 10e6 | 50 μA | 94000 | 91600 | 85600 | 70400 | 84400 |
|  | 500 μA | 46400 | 45600 | 27200 | 2000 | 400 |

Table 4 below shows the efficacy of treatment according to the present invention at current levels of 50 μA or 500 μA for 5, 10, 20 and 30 minute durations for bacterial cultures ranging from $10^4$ to $10^6$ CFU of *Fusobacterium nucleatum* in saliva.

TABLE 4

In Vitro Efficacy of Device Against Fusobacterium nucleatum in Saliva

| CFU | μA | 0 Min | 5 Min | 10 Min | 20 Min | 30 Min |
|---|---|---|---|---|---|---|
| 10e4 | 50 μA | 1480 | 1480 | 1560 | 680 | 880 |
|  | 500 μA | 2360 | 2360 | 1720 | 1240 | 1080 |
| 10e5 | 50 μA | 19600 | 19600 | 15200 | 14400 | 14000 |
|  | 500 μA | 18000 | 17200 | 14400 | 11200 | 10800 |
| 10e6 | 50 μA | 348000 | 112000 | 120000 | 72000 | 68000 |
|  | 500 μA | 156000 | 128000 | 124000 | 32000 | 28000 |

Table 5 below shows the efficacy of treatment to the present invention at current levels of 50 μA or 500 μA for 5, 10, 20 and 30 minute durations for bacterial cultures ranging for $10^5$ CFU of *Porphyromonas gingivalis* in a saline solution.

TABLE 5

In Vitro Efficacy of Device Against Porphyromonas gingivalis in Saline

| CFU | μA | 0 Min | 5 Min | 10 Min | 20 Min | 30 Min |
|---|---|---|---|---|---|---|
| 10e4 | 50 μA | 3440 | 2040 | 2720 | 1640 | 1640 |
|  | 500 μA | 2440 | 2120 | 2200 | 1880 | 1840 |

Thus, this method and corresponding apparatus are able to achieve multiple prophylactic, therapeutic, and regenerative effects whose combination was not previously known or available in the art. Namely, these effects are: promotion of oral osteogenesis, destruction or disabling of oral microbes, gingival tissue regeneration, reduction and prevention of the formation of oral biofilms, caries prevention, increased oral vasodilation and oral blood flow, treatment of common oral conditions such as gingivitis and periodontitis, treatment of systemic diseases and conditions correlated with oral pathogens, and generally improved oral hygiene.

These effects are accomplished by the delivery of direct current to the gingiva through a plurality of electrodes in direct contact with the lingual and buccal gingival surfaces. The electrodes may be fashioned out of any electrically-conductive material, including but not limited to metals such as silver, stainless steel, copper, gold, platinum, palladium, aluminum, an alloy thereof, electrically-conductive nano-tubes, carbonized rubber, electrically-conductive silicone, or electrically-conductive polymers. The electrodes may be composed of the same or of differing materials. These electrodes fit snuggly against the lingual and buccal sides of the gingiva and make direct contact with each side of the gingiva to pass direct current electricity across the teeth and neighboring gingival tissues.

The electrodes on each side (lingual or buccal) of the gingiva are of the same polarity. Electrodes on opposite sides of the gingiva are of the opposite polarity. This allows the current to flow across the teeth and gums to the electrodes positioned on the transverse gingiva to complete the electrical circuit. Put another way, all electrodes on the lingual side of the gingiva will be completely anodic or completely cathodic. All electrodes on the buccal surfaces of the gingiva, transverse the lingual surfaces of the gingiva, would have the opposite polarity. The polarization of these electrodes may be reversed during treatment or in between treatments.

The mandibular and maxillary gingiva each have a set of a plurality of polarized electrodes as previously described. This allows for treatment of both the maxillary and mandibular periodontium either simultaneously or in isolation. The maxillary and mandibular sets of electrodes may be powered by two different adjustable power supplies or by the same adjustable power supply.

Electrical conductors then connect these electrodes to an adjustable power supply. All of the anodic electrodes will connect to the positive pole of the power supply and all of the cathodic electrodes will connect to the negative pole of the power supply. The adjustable power supply is capable of delivering a stable, direct current in the approximate range of 1 to 500 microamperes. The preferred current setting for most treatments is in the approximate range of 50 to 250 microamperes.

In order to increase conductivity in the tissues adjacent to the electrodes, an ionic or colloidal liquid or gel may be used as a conductive medium to decrease electrical resistance in the mouth. This medium would be placed along any desired areas of desired electrical contact, such as the teeth, gums, or surrounding oral tissues. Examples of such a medium would include, but not be limited to, colloidal silver gel, liquid colloidal silver, colloidal copper gel, liquid colloidal copper, colloidal gold gel, liquid colloidal gold, saline gel, liquid saline or any combination thereof.

Colloidal silver, in whole or in combination, has great promise not only in increasing electrical current flow, but also in offering additional bactericidal benefits. Colloidal silver, in concentrations as little as five parts per million, is known to be bactericidal by inhibiting a bacterium's production of adenosine triphosphate.

This conductive medium may also contain dietary supplements including, but not limited to, oil of oregano. Oil of oregano is believed to have many health benefits and may also be microbicidal. Such microbicidal properties would be effective in treating common oral infections and diseases as well as aiding in preventative oral care.

This conductive medium may also contain teeth whitening agents. This would allow for the addition of teeth whitening to the list of benefits offered by an embodiment of this invention. A whitening agent that is catalyzed by direct current electricity could be included and may even offer reduced teeth whitening treatment times when compared with nonelectrically-catalyzed whitening agents.

Artificial or natural flavorings may also be added to this conductive medium to offer a more appealing taste to the user, similar to the method of flavoring dental fluoride treatments. This flavoring would mask any unpleasant tastes from the ingredients of the conductive medium or as well as any taste of the mouthpiece or electrodes themselves.

FIG. 1 shows one embodiment of a treatment apparatus according to this invention. A user input device 120 is connected to a microcontrolled direct current power supply 110. This input device 120 may include, but not be limited to potentiometer dials, push buttons, switches, toggles, etc. User input device 120 allows the patient to control various aspects of the treatment including but not limited to power on or off, output current levels, treatment program selection, treatment duration, treatment reminders, polarity, etc. Input device 120 may also be used to run pre-programmed treatment regimens as described by this method targeted at specific pathogens, including but not limited to, *S. oralis*, *P. gingivalis*, and *F. nucleatum*. Microcontrolled power supply 110 reads the state of input device 120 and adjusts the output current to compensate for the continually varying resistance across cathodic electrodes 140 and anodic electrodes 150.

An optional user feedback device 130 is shown in FIG. 1 connected to microcontrolled power supply 110. Feedback device 130 may contain various methods and devices capable of relaying treatment information to the user. Feedback device 130 could include, but not be limited to an LCD display, LCD matrix display, color LCD displays, indicator LEDs, LED bar graphs, LED segment displays, OLED displays, audio speakers, vibrating devices, or any combination thereof. Feedback device 130 offers the user information including, but is not limited to, output current level, treatment time elapsed, treatment time remaining, date, time of day, battery power level, treatment reminder indicators or sound alarms, recharging indicators, etc. Feedback device 130 also provides information regarding any state change from input device 120. This allows the user to receive information on how his/her input is affecting the treatment. Feedback device 130 is not required for the operation of this embodiment of the treatment apparatus and may be omitted.

Microcontrolled power supply 110 contains a microcontroller 112 and a direct current power source 116. Microcontroller 112 is electrically connected to input device 120 and is capable of reading the device's state(s). Microcontroller 112, upon reading these state(s), is able to dynamically adjust the output of power source 116. This allows the user to control the level of current generated by the power source 116. Microcontroller 112 is also connected to an optional user feedback device 130. Microcontroller 112 is able to output information related to the treatment duration, current timer status, current levels, and other information to feedback device 130. Microcontroller 112 also has timing capabilities, represented by timer 114, that allow for limiting treatment time based on some predetermined treatment duration. Timer 114 is also used to output the elapsed treatment time to feedback device 130, if present. The user is able to input desired treatment parameters such as treatment duration, treatment current levels, etc. to microcontroller 112 by way of input device 120.

The programmable nature of microcontroller 112 allows for advanced functionality not present in other oral electrical treatment devices. For example, the software on microcontroller 112 could be programmed to run a predetermined treatment regimen. This treatment regimen could include but not be limited to such factors as: treatment duration, targeted pathogen, treatment current levels, treatment time-of-day, treatment reminders, etc. This treatment regimen could also be programmed by a dental professional by way of input device 120 so that a patient's treatment may be simplified and guaranteed to follow set parameters.

Cathodic electrodes 140 are connected to the positive pole of power source 116 and anodic electrodes 150 are connected to the negative pole of power source 116. These electrodes are placed in direct contact with the gingiva, mounted transversely from one another. This allows a current flow from cathodic electrodes 140 to the gingival tissues, surrounding teeth, boney structures, and connected mouth tissues to anodic electrodes 150 mounted on the transverse gingiva and then back to power supply 110, forming a complete circuit.

Power source 116 may be any known device capable of delivering an adjustable direct electrical current. This includes, but is not limited to disposable batteries, rechargeable batteries, AC-DC power converter, etc. Microcontroller 112 is able to regulate the current output of power source 116 by a known method of electrical current control. Power supply 116 is capable of delivering a direct current of between 1 and 500 microamperes, with an approximate range of 50 to 250 microamperes used for most treatments. Microcontroller 112 is also able to reverse the polarity of the cathodic electrodes 140 and anodic electrodes 150 by controlling the output of power source 116. This allows for dynamic changing of electrode polarity during treatment. Microcontroller 112 is also programmable to allow for pulsed application of direct current across the gingiva.

Figure 2:
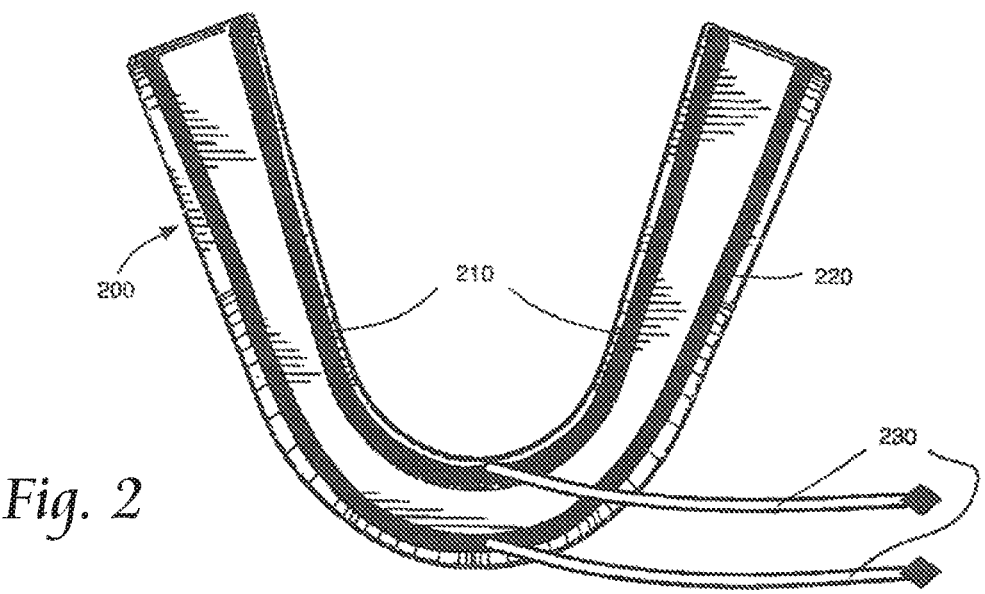
FIG. 2 shows a top-down view of another embodiment that includes a mouthpiece with two continuous electrodes and associated conductors.

FIG. 2 shows a top-down view of another embodiment of the treatment apparatus. In this embodiment, a mouthpiece unit 200, known in the art, has two electrodes attached to or embedded in it, and is worn in the mouth. A single lingual gingiva electrode 210 fits snugly against the lingual gingival tissue of the mouth. A single buccal gingiva electrode 220 is attached to or embedded in mouthpiece 200 so that it is transverse from the lingual gingiva electrode 210 and fits snugly against the buccal gingival tissues of the mouth. Two electrical conductors 230 connect electrodes 210 and 220 to an adjustable current power supply, of whose embodiment may be similar to that of 110 or that of FIG. 3. Electrical conductors 230 are insulated so that a short circuit does not occur inside or outside of the mouth. Electrical conductors 230 are shown as attached to the anterior of mouthpiece 200, but may be electrically connected to electrodes 210 and 220 at any point along mouthpiece 200, so long as electrical conductors 230 are not attached to the same electrode. Electrical conductors 230 may also be partially or wholly composed of an electrically conductive polymer.

Figure 3:
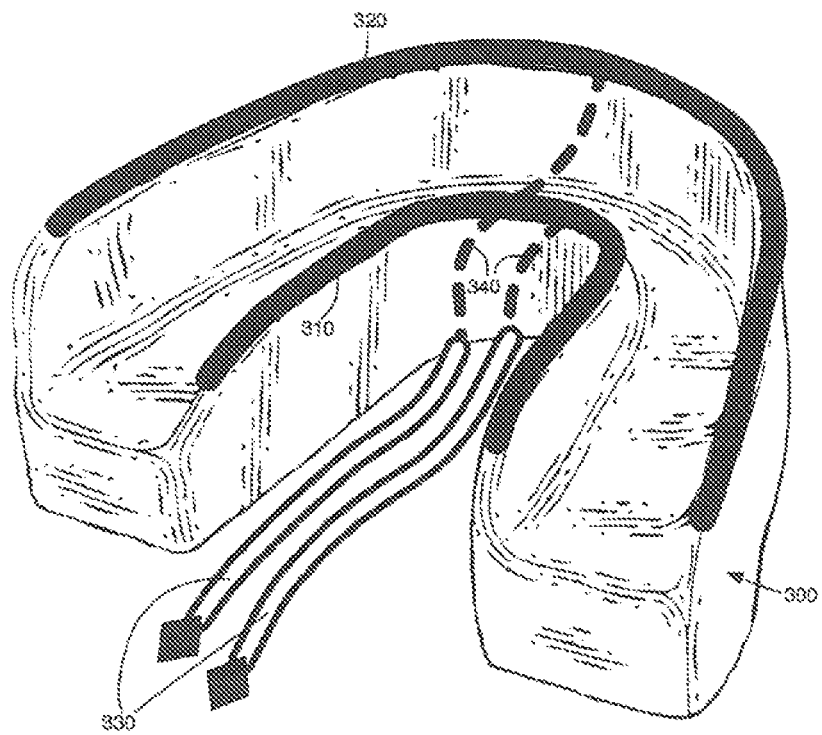
FIG. 3 shows a perspective view of the same embodiment of FIG. 2, with two electrodes embedded in a mouthpiece.

FIG. 3 shows a perspective view of the same type of embodiment shown in FIG. 2. A mouthpiece 300 has a lingual gingiva electrode 310 and a buccal gingiva electrode 320 attached to or embedded it. Electrodes 310 and 320 span the lingual and buccal gingival surfaces of the mouth, respectively. A set of embedded electrical conductors 340 are connected to electrodes 310 and 320 on one end and on the other end to a set of conductors to the power supply 330.

Conductors 340 are embedded in the mouthpiece material and are electrically insulated. Conductors 330 then connect to the positive and negative poles of a direct current power source, similar to that of 110 or FIG. 6.

Figure 4:
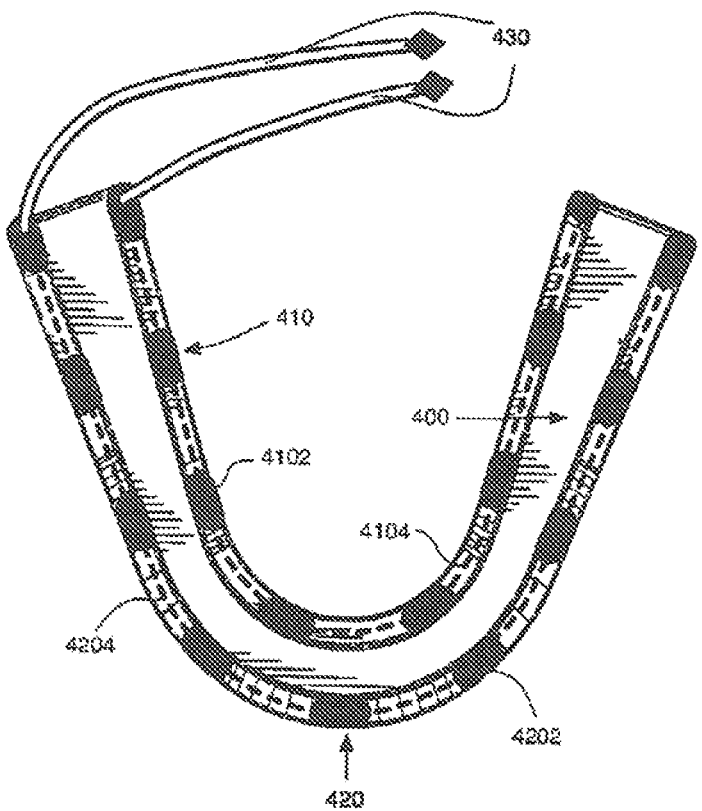
FIG. 4 offers a top-down view of another embodiment similar to FIG. 2 that includes a mouthpiece, but with a plurality of discrete electrodes.

FIG. 4 presents another embodiment similar in nature to that of FIGS. 2 and 3. In this embodiment, electrode sets are attached to or embedded in a mouthpiece unit 400. A set of lingual gingiva electrodes 410 are affixed to or embedded in mouthpiece 400. Electrode set 410 comprises a plurality of discrete lingual gingiva electrodes 4102, which are electrically connected by embedded electrical conductors 4104. Conductors 4104 are insulated and are embedded in or attached to mouthpiece 400. Likewise, a set of buccal gingiva electrodes 420 are affixed to or embedded in mouthpiece 400 transverse of electrode set 410. Electrode set 420 comprises a plurality of discrete lingual gingiva electrodes 4202, which are electrically connected by embedded electrical conductors 4204. Conductors 4204 are insulated and are embedded in or attached to mouthpiece 400. This embodiment allows for multiple, discrete points of electrical contact within the mouth. In FIG. 4, conductors to the power supply 430 are shown as attached to the posterior electrodes in mouthpiece 400. However, conductors 430 may be electrically connected to any point of electrode sets 410 and 420, so long as conductors 430 are not connected to the same electrode set. Conductors 430 then connect to the positive and negative poles of a direct current power source, similar to that of 110 or FIG. 6.

Figure 5:
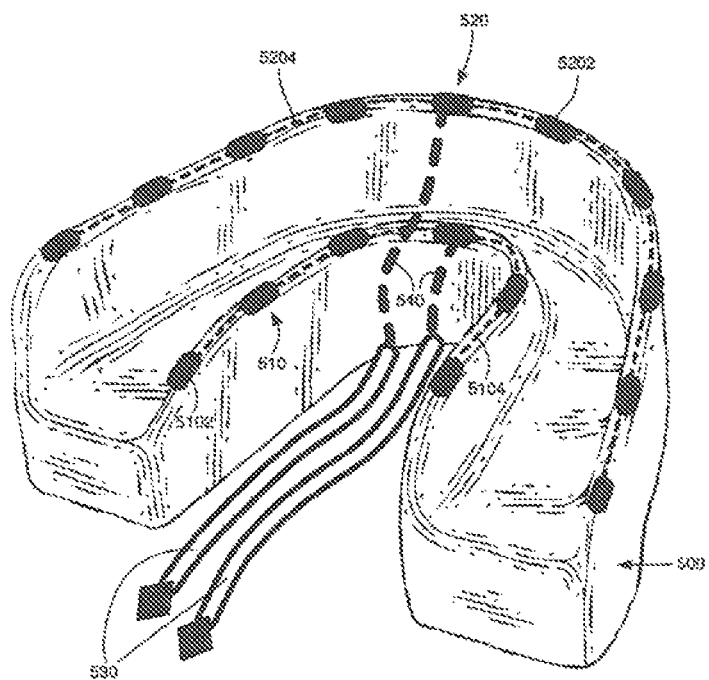
FIG. 5 provides a perspective view of an additional embodiment similar to FIG. 4 with a plurality of electrodes that are electrically connected by embedded conductors.

FIG. 5 offers a perspective view of an embodiment similar to FIG. 4. A lingual gingiva electrode set 510 and a buccal gingiva electrode set 520 are attached to or embedded in a mouthpiece 500. Electrode set 510 comprises a plurality of lingual gingiva electrodes 5102 that are electrically connected by embedded electrical conductors 5104. Conductors 5104 are electrically insulated and are embedded in or attached to mouthpiece 500. Similarly, electrode set 520 comprises a plurality of buccal gingiva electrodes 5202 that are electrically connected by embedded electrical conductors 5204. Conductors 5204 are electrically insulated and are embedded in or attached to mouthpiece 500. Electrode set 520 is mounted transverse of electrode set 510 to allow direct current to flow across the tissue of the teeth and gums. Electrode sets 510 and 520 are connected to conductors to the power supply 530 by way of embedded electrical conductors 540. Conductors 540 are electrically-insulated and are embedded in mouthpiece 500. Conductors 530 then connect to the positive and negative poles of a direct current power source, similar to that of 110 or FIG. 6.

Figure 6:
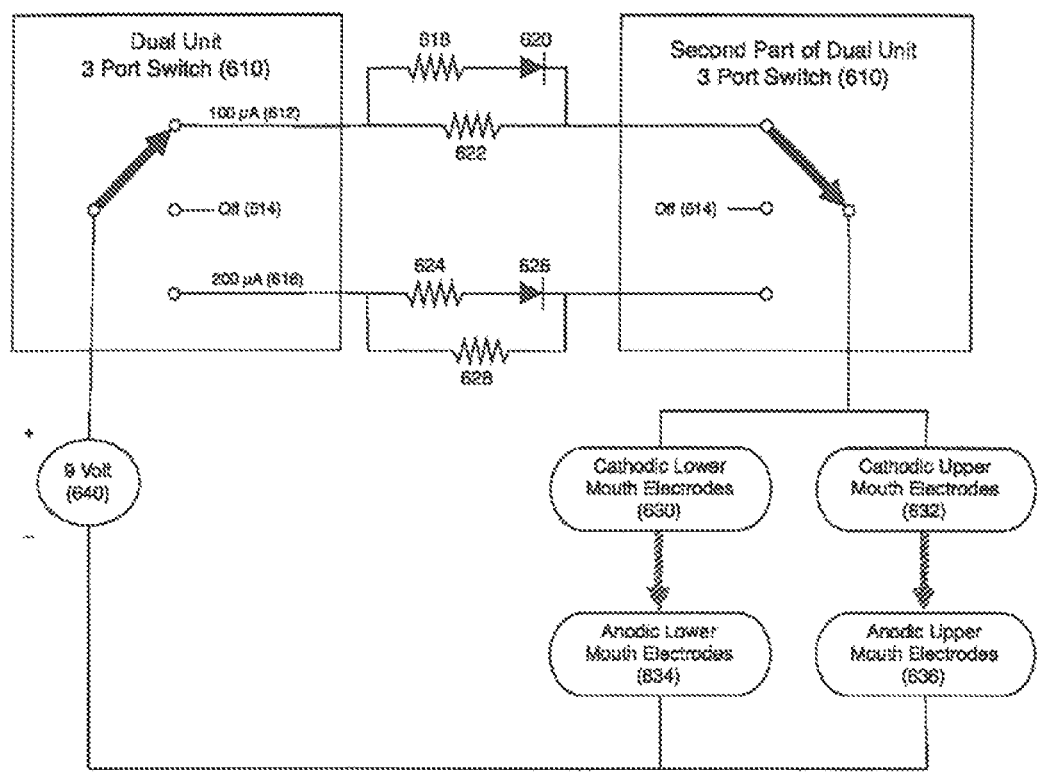
FIG. 6 shows an additional embodiment of a device according to the present invention with an analog power supply using a dual unit, three-port switch.
Figure 7:
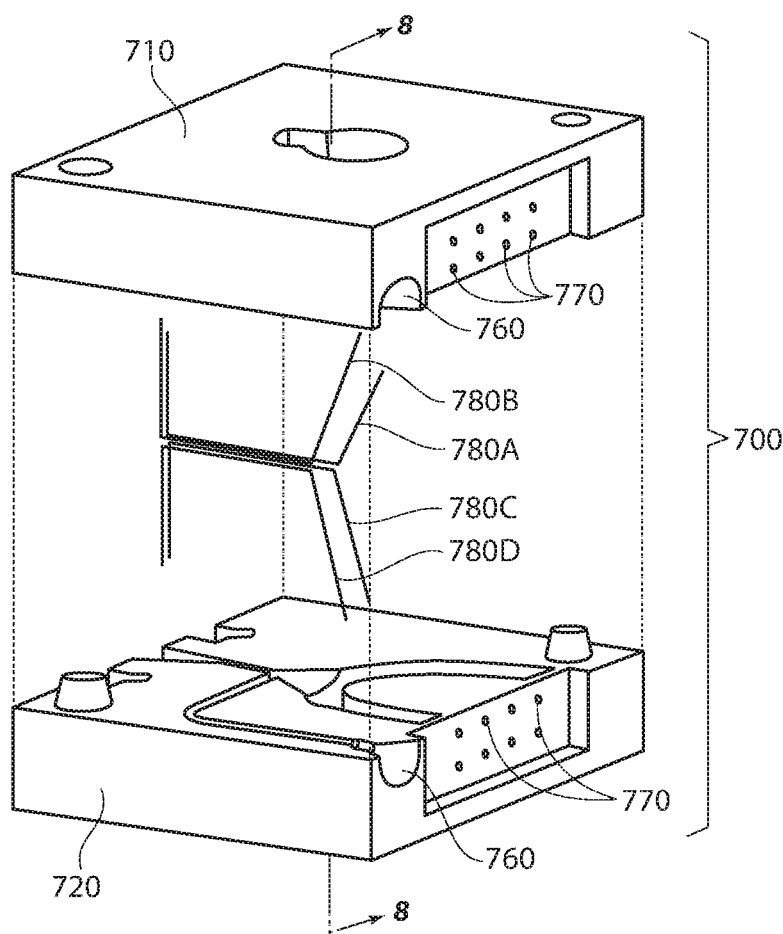
FIG. 7 is an exploded view of a first mold for molding a mouthpiece according to the present invention.

FIG. 6 presents another embodiment of an adjustable direct current power source used to supply direct current to a plurality of oral electrodes. This particular circuit design is capable of delivering a steady current regardless of moderate fluctuations in the resistance between the electrodes. The circuit uses a 9-volt power supply 640, which could be a disposable battery, a rechargeable battery, an AC-to-DC converter, or any other suitable 9-volt power source. A dual unit, three-port switch 610 is used to select the current level in the circuit. The three options of the switch circuit are power off 614, 100 µA 612, or 200 µA 616. Switch option 614 simply does not complete a circuit, preventing current from flowing. Switch option 612 comprises a 332 kΩ resistor 618 in series with a 2 volt LED 620. These two components are in parallel with a 48.7 kΩ resistor 622 to provide a 100 microamp current. The Switch option 616 comprises a 665 kΩ resistor 624 in series with a 2 volt LED 626. These two components are in parallel with a 97.6 kΩ resistor 628 to provide a 200 microamp current. Cathodic upper mouth electrodes 630 and cathodic lower mouth electrodes 632 are in parallel with each other and are electrically connected to the output of switch 610. Electrical current then travels from power supply 640 to these electrodes, through the gingival tissues of the mouth to anodic upper mouth electrodes 636 and anodic lower mouth electrodes 634 and finally back to power supply 640. This circuit design will allow moderate and reasonable fluctuations in the resistance across the electrodes and prevent over driving the circuit should the resistance in the mouth vary.

In another embodiment of this invention or in combination with those previously described, an ionic or colloidal medium in the form of a liquid or a gel may be used to decrease electrical resistance in the mouth and to facilitate a more even current distribution across oral electrodes. Any combination of one or more ionic or colloidal compounds may be used. Examples of such a medium would include, but not be limited to, colloidal silver gel, liquid colloidal silver, colloidal copper gel, liquid colloidal copper, colloidal gold gel, liquid colloidal gold, saline gel, liquid saline or any combination thereof. Artificial or natural flavorings may be added to this medium to offer a more appealing taste to the user. The medium may also contain dietary supplements including, but not limited to, oil of oregano. This medium may also contain teeth-whitening chemical agents. A whitening agent that is catalyzed by the direct current would be most effective in this ionic or colloidal medium.

In yet another embodiment, microcontrolled power supply 110 would be miniaturized and be physically attached to or embedded in a mouthpiece similar to 200, 300, 400, or 500. This would allow for an all-in-one unit that would fit inside the user's mouth. In this embodiment, power source 116 would have to be of small physical size. One of many possible options is a watch-type battery or other small, portable power source. This circuitry would then be encased in a waterproof manner in the material of the mouthpiece itself. Input device 120 and feedback device 130 would be waterproofed and protected from any kind of electrical shorting, as well.

Thus the reader will see that at least one embodiment addresses a desired need in the oral hygiene and dental fields to concurrently treat common oral diseases and conditions in a more effective, less invasive, and less expensive manner. These embodiments promote general oral hygiene, reduce oral biofilm, treat periodontal diseases such as gingivitis and periodontitis, kill oral microbes including bacteria and thus preventing cavities and tooth decay, increase vasodilation and blood flow in oral tissues, promote gingival tissue regeneration, foster osteogenesis in the boney structures of the teeth, mouth, and related areas, treat systemic diseases related to oral pathogens, and treat other periodontal and oral maladies through the non-invasive application of weak direct current electricity to the surfaces in the oral cavity.

While our above descriptions contain many specificities, these should not be construed as limitations on the invention, but rather as an exemplification of several preferred embodiments thereof. Many other variations are possible. For example, electrodes may be attached directly to the gingiva without the use of a mouthpiece, perhaps using an electrically-conductive paste. Or electrodes may be placed in contact with tissues neighboring the gingiva, such as the teeth or tissues of the cheek, instead of directly on the gingiva to accomplish the same result. Another example would be replacing LEDs 626 and 620 from FIG. 6 with standard diodes to achieve the same resultant circuit. Overall, the circuitry from FIGS. 1 and 6 could be altered in many ways to deliver the same electrical current to the oral electrodes.

In some cases dental procedures can break up oral bacterial colonies found in biofilms and introduce bacteria into the bloodstream causing bacteremia and other infections. It is further contemplated that it may be desirable to utilize a mouthpiece according to the present invention immediately prior to performing a dental procedure. The mouthpiece according to this invention may be used by the patient either at home or in the dental office. In this manner, the living bacteria in the patient's mouth, both supra- and sub-gingival, can be reduced prior to the procedure and the risk of bacteremia and other infections will be reduced. For example, and not by way of limitation, a mouthpiece according to the present invention may be utilized prior to a dental prophylaxis or a scaling and root planning procedure in a dental office to reduce the risks of introducing bacteria into the patient's blood stream. Such a pre-procedural treatment would be used for approximately 10 to 20 minute with a current level ranging from 50 µA to 500 µA and would be timed to conclude immediately before the procedure.

A mouthpiece according to the present invention may also be utilized following a clinical procedure as prevention for infections, for scenarios including but not limited to post-extraction or post-implantation infection prevention. Such a post-procedural treatment would last for approximately 10 to 20 minutes with a current ranging from 50 µA to 500 µA. This procedure may then be repeated at home by the patient one or more times a week until the risk of infection has passed.

Prevention of Systemic Disease

It is contemplated that a mouthpiece according to the present invention may be used to prevent or treat systemic diseases as will be outlined in more detail below. The method according to the present invention has been shown to be effective in reducing the amount of oral bacteria, specifically *F. nucleatum*, *P. gingivalis*, and *S. oralis*.

1. Cardiovascular Disease

It is contemplated that use of a mouthpiece according to the present invention may be used to reduce microbial burdens caused by the translocation of oral bacteria, including but not limited to *S. oralis*, *P. gingivalis*, and *F. nucleatum*, from the gingival tissues to the rest of the body and also decrease the amount of inflammatory mediators produced by oral bacteria. Further, by reducing *F. nucleatum*, it is contemplated that the ability of *P. gingivalis* to invade host cells will be lessened and thus diminishing the development of bacteremia that has been linked with the initiation/worsening of atherosclerosis and coronary heart disease.

It is contemplated that a mouthpiece according to the present invention may be used according to a predetermined treatment regimen to prevent, treat and/or mitigate cardiovascular disease. In the predetermined treatment regimen, the patient will wear a mouthpiece according to the present invention for a predetermined amount of time at a predetermined current level and at predetermined time intervals. It is further contemplated that the specific treatment regimen may be determined based on the bacterial levels present in a patient. According to one embodiment of the invention, the treatment regimen would consist of a patient wearing a mouthpiece according to the present invention for 20 minutes once per day at a current level of 500 µA. For acute cardiovascular conditions, this treatment may continue on a daily basis until the conditions is resolved. For chronic cardiovascular disease, this treatment may be repeated a few times a week on a continuing basis.

2. Still Birth

It is further contemplated that a treatment with a mouthpiece according to the present invention according to a predetermined treatment protocol would reduce the oral population of *F. nucleatum* associated with periodontal disease and thus prevent, treat and/or mitigate still birth. In turn, this reduction would lessen the likelihood of *F. nucleatum* translocating from the oral cavity into the bloodstream, where it could then migrate into the placenta and colonize. It is contemplated that a mouthpiece according to the present invention may be used according to a predetermined treatment regimen to prevent still birth. In the predetermined treatment regimen, the patient will wear a mouthpiece according to the present invention for a predetermined amount of time at a predetermined current level and at predetermined time intervals. It is further contemplated that the specific treatment regimen may be determined based on the bacterial levels present in a patient. According to one embodiment of the invention, the treatment regimen would consist of a patient wearing a mouthpiece according to the present invention for 20 minutes once per day at a current level of 500 µA for the duration of the pregnancy. The treatment parameters outlined above have been demonstrated to be highly efficient at reducing levels of *S. oralis* and *F. nucleatum* at inoculation sizes of $10^7$ colony-forming units (CFU).

3. Diabetes

It is contemplated that a mouthpiece according to the present invention according to a predetermined treatment protocol may be used to prevent, treat and/or mitigate diabetes by causing a reduction of *S. oralis* in the oral cavity and consequently reduce the amount of serum markers of inflammation produced by bacterial infections. In the predetermined treatment regimen, the patient will wear a mouthpiece according to the present invention for a predetermined amount of time at a predetermined current level and at predetermined time intervals. It is further contemplated that the specific treatment regimen may be determined based on the bacterial levels present in a patient. According to one embodiment of the invention, the treatment regimen would consist of a patient wearing a mouthpiece according to the present invention for 20 minutes once per day at a current level of 500 µA to effectively reduce oral levels of *S. oralis* that in turn will lower the amount of systemic inflammatory markers. This treatment may be repeated multiple times a week on an ongoing basis to help reduce inflammatory markers.

4. Pyogenic Liver Abscess

It is contemplated that a mouthpiece according to the present invention according to a predetermined treatment protocol may be used to prevent, treat and/or mitigate pyogenic liver abscess by causing a reduction of *F. nucleatum*. Specifically, it is contemplated that treatment with a mouthpiece according to the present invention would reduce bacterial levels and may stop *F. nucleatum* and other oral bacteria species from traveling to the liver and reduce overall bacteremia. In the predetermined treatment regimen, the patient will wear a mouthpiece according to the present invention for a predetermined amount of time at a predetermined current level and at predetermined time intervals. It is further contemplated that the specific treatment regimen may be determined based on the bacterial levels present in a patient. According to one embodiment of the invention, the treatment regimen would consist of a patient wearing a mouthpiece according to the present invention for 20 minutes once per day at a current level of 500 µA to effectively reduce oral levels of *F. nucleatum* which may prevent any bacteria from being transported from the oral cavity systemically. This treatment may be repeated multiple times per week until the abscess is reduced.

5. Osteomyelitis

It is contemplated that a mouthpiece according to the present invention according to a predetermined treatment protocol may be used to prevent, treat and/or mitigate osteomyelitis by causing a reduction of *F. nucleatum*. In the predetermined treatment regimen, the patient will wear a mouthpiece according to the present invention for a predetermined amount of time at a predetermined current level and at predetermined time intervals. It is further contemplated that the specific treatment regimen may be determined based on the bacterial levels present in a patient. According to one embodiment of the invention, the treatment regimen would consist of a patient wearing a mouthpiece according to the present invention for 20 minutes per treatment at a current level of 500 µA to effectively reduce oral levels of *F. nucleatum* bacteria and prevent any bacteria from being transported from the oral cavity systemically. This treatment may be used in conjunction with or separate from standard antibiotic-based treatments for osteomyelitis. When used in conjunction with antibiotics, treatment will normally continue for approximately 29 to 42 days. When used separately from antibiotics, this treatment may be used once a day for a few months for acute conditions, or a few times a week on a continuing basis for chronic conditions.

6. Arthritis

It is contemplated that a mouthpiece according to the present invention according to a predetermined treatment protocol may be used to prevent, treat and/or mitigate arthritis by causing a reduction of *F. nucleatum*. In the predetermined treatment regimen, the patient will wear a mouthpiece according to the present invention for a predetermined amount of time at a predetermined current level and at predetermined time intervals. It is further contemplated that the specific treatment regimen may be determined based on the bacterial levels present in a patient. According to one embodiment of the invention, the treatment regimen would consist of a patient wearing a mouthpiece according to the present invention for 20 minutes once per day at a current level of 500 µA to effectively reduce oral levels of *F. nucleatum* bacteria and prevent any bacteria from being transported from the oral cavity and translocating to the synovial fluid and reducing the associated inflammation. This treatment may be repeated multiple times per week on a continual basis for this type of chronic condition.

Reducing Bio Film and Preventing Bio Film Formation

It is contemplated that a mouthpiece according to the present invention according to a predetermined treatment protocol may be used to prevent, treat and/or mitigate oral biofilm by causing a reduction of *F. nucleatum*, *P. gingivalis*, and/or *S. oralis*, all of which are involved in oral biofilm formation. In the predetermined treatment regimen, the patient will wear a mouthpiece according to the present invention for a predetermined amount of time at a predetermined current level and at predetermined time intervals. It is further contemplated that the specific treatment regimen may be determined based on the bacterial levels of specific bacterial species present in a patient. According to one embodiment of the invention, the treatment regimen would consist of a patient wearing a mouthpiece according to the present invention for 20 minutes once per day at a current level of 500 µA to effectively reduce oral levels of *F. nucleatum* bacteria to prevent further biofilm formation caused by *F. nucleatum* and to reduce the viability of existing biofilm colonies of *F. nucleatum*.

According to another embodiment of this invention, the treatment regimen would consist of a patient wearing a mouthpiece according to the present invention for 20 minutes once per day at a current level of 50 µA to effectively reduce oral levels of *P. gingivalis* bacteria to prevent further biofilm formation caused by *P. gingivalis* and to reduce the viability of existing biofilm colonies of *P. gingivalis*.

Furthermore, according to another embodiment of this invention, the treatment regimen would consist of a patient wearing a mouthpiece according to the present invention for 20 minutes once per day at a current level of 500 µA to effectively reduce oral levels of *S. oralis* bacteria to prevent further biofilm formation caused by *S. oralis* and to reduce the viability of existing biofilm colonies of *S. oralis*.

These treatments for biofilm reduction and prevention may be repeated on a daily basis for a three to six weeks for acute biofilm-based issues or may be repeated once or more per week on a continuing basis for chronic biofilm issues.

Treatment of Non-Human Animals

Systems and methods according to the present invention may be used to reduce oral bacteria and/or biofilm, as well as to treat systemic diseases that may be associated with oral bacteria, in non-human animals, such as dogs, cats, sheep, horses, cows, pigs, etc.

For instance, periodontal disease is one of the most common health problems affecting dogs (>75%). The prevalence of periodontal disease has been found to increase age but decrease with body weight. Various systemic diseases have been suggested as a strong co-factor for periodontal disease in animals, just as in humans. It has been suggested that periodontal disease could have a causal relationship with systemic diseases in both humans and animals. For dogs, and animals in general, periodontitis is a recurrent and persistent disease and exposes the host to negative systemic effects over an extended period of time, e.g. several years.

It has been observed that, over the course of several years, frequent exposure of bacteremia as a result of minor trauma at sites of periodontal inflammation may cause infection or induce inflammation at distant sites with the body. The pathogenesis of periodontal disease in dogs has been linked with gram-negative anaerobic bacteria upon accumulation within the gingival sulcus causing inflammation and the formation of periodontal pockets. The inflammatory response to periodontal pathogens promotes the formation and release of endotoxins and inflammatory cytokines that can decrease functions of vital organs over time. It has been suggested that systemic diseases may be associated with periodontal disease in dogs, including chronic bronchitis, pulmonary fibrosis, endocarditis, interstitial nephritis, glomerulonephritis, and hepatitis.

Periodontal organisms present in dogs with periodontitis have been isolated and identified previously. For instance, the following periodontal pathogens have been found to be associated with periodontal disease in dogs: *P. gingivalis* (64% of periodontitis-positive dogs), *C. rectus*, *A. actinomycetemcomitans*, *P. intermedia*, *T. forsythensis*, *F. nucleatum* (4% of periodontitis-positive dogs), *E. corrodens*, *P. denticanis*, *P. gulae*, *P. salivosa*. Recommended treatments using systems and/or methods according to the present invention to treat and/or prevent periodontal disease by reducing or controlling such types of bacteria, may include a predetermined time, such as 20 minutes, of oral secretions and/or tissue (i.e., saliva, lingual tissue, dental tissue, gingival tissue, periodontal tissue, and/or oral mucosa tissue) exposure to an electrical current (alternating or direct current, constant or pulsed) level of between about 50 microamps (µA) and about 500 microamps (µA). Devices according to the present invention have been shown to be effective at reducing the count of bacterial species in this current range.

As with dogs, periodontal disease in cats is associated with local inflammation and is purported to influence and induce systemic responses and organ function in distal sites. One of the common oral pathogens found in the oral cavity of cats is *P. gingivalis*. Studies have demonstrated that indeed measurable systemic changes arise during the progression of periodontal disease, such as increased levels of serum IgG. Further, these levels could be altered with periodontal treatment. Recommended treatments using systems and/or methods according to the present invention to treat and/or prevent periodontal disease in cats by reducing or controlling such types of bacteria, may include a predetermined time, such as 20 minutes, of oral tissue exposure to an electrical current (alternating or direct current, constant or pulsed) level of between about 50 microamps ($\mu A$) and about 500 microamps ($\mu A$). Devices according to the present invention have been shown to be effective at reducing the count of such bacterial species in this current range.

Periodontitis may also be found in sheep, also referred to as "broken mouth", and is associated with severe degradation of periodontal collagen, loss of alveolar bone, appearance of periodontal pockets and premature tooth loss. Although morphological and histological differences exist between the periodontium of sheep and humans, the histopathological appearance is similar in periodontal disease, including the role that *P. gingivalis* plays in the progression of the disease. Recommended treatments using systems and/or methods according to the present invention to treat and/or prevent periodontal disease in sheep by reducing or controlling such types of bacteria, may include a predetermined time, such as 20 minutes, of oral tissue exposure to an electrical current (alternating or direct current, constant or pulsed) level of between about 50 microamps ($\mu A$) and about 500 microamps ($\mu A$). Devices according to the present invention have been shown to be effective at reducing the count of such bacterial species in this current range.

Cardiovascular-related conditions may also exist in non-human animals. For instance, there has in dogs been revealed an association between periodontal disease severity and risk of cardiovascular-related conditions, such as endocarditis and cardiomyopathy. Endocarditis is a result of infection and inflammation of the heart endothelium, or tissue lining the inner surface of the heart valves and can be caused by various microorganisms. Cardiomyopathy is characterized by an enlarged heart that does not function properly. Both diseases carry a poor prognosis based on the severity of the case. For dogs, it has been found that the risk of endocarditis was 6-fold higher in dogs with stage 3 periodontal disease than it was for healthy dogs and for cardiomyopathy it was about 4-fold. Cardiac disease progression may be affected by the presence and/or prevalence of certain oral bacteria, including *S. oralis*, *F. nucleatum*, and *P. gingivalis*. Recommended treatments using systems and/or methods according to the present invention to treat and/or prevent cardiac disease by reducing or controlling such types of bacteria, may include a predetermined time, such as 20 minutes, of oral tissue exposure to an electrical current (alternating or direct current, constant or pulsed) level of between about 50 microamps ($\mu A$) and about 500 microamps ($\mu A$). Devices according to the present invention have been shown to be effective at reducing bacterial burden of all three species in this current range.

In addition to cardiac disease, a prior retrospective longitudinal study has established a relationship between periodontal disease and chronic kidney disease (CKD). The hazard ratio of CKD in dogs, in conjunction with increased serum creatinine and blood urea nitrogen concentrations, has been shown to increase, with increasing severity of periodontal disease, from stage 1 to stage 4, thereby establishing a significant positive association between periodontal disease and CKD.

Both *F. nucleatum* and *P. gingivalis* are common oral pathogens presented in dogs, and may be linked to kidney disease. Accordingly, reduction of such pathogens may be used as a treatment or prevention thereof. Recommended treatments using systems and/or methods according to the present invention to treat and/or prevent kidney disease by reducing or controlling such types of bacteria, may include a predetermined time, such as 20 minutes, of oral tissue exposure to an electrical current (alternating or direct current, constant or pulsed) level of between about 50 microamps ($\mu A$) and about 500 microamps ($\mu A$). Devices according to the present invention have been shown to be effective at reducing the count of such bacterial species in this current range.

Non-human animal diabetes may also be treated and/or prevented using systems and methods according to the present invention. In humans, as stated, there is an established link between diabetes mellitus and periodontal disease, and such a relationship has been suspected in veterinary medicine. One prior study has demonstrated that blood glucose concentrations are increased in relation to attachment loss and periodontal disease state in dogs. Additionally, these levels decreased following periodontal disease treatment.

The *S. oralis* bacterium has been associated with severe periodontitis and diabetes. Recommended treatments using systems and/or methods according to the present invention to treat and/or diabetes by reducing or controlling such types of bacteria, may include a predetermined time, such as 20 minutes, of oral tissue exposure to an electrical current (alternating or direct current, constant or pulsed) level of between about 50 microamps ($\mu A$) and about 500 microamps ($\mu A$). Devices according to the present invention have been shown to be effective at reducing the count of such bacterial species in this current range. Such a reduction may help combat high levels of blood glucose.

Furthermore, systems and methods according to the present invention may be used to affect (preferably reduce and/or eliminate) the number of oral bacteria transferred between animals of different species, such as between a pet and its owner. It is well established that oral bacteria, including periodontal pathogens, can be transmitted between mothers and their children simply through everyday close contact. Therefore, it is not unfounded that transmission of such bacteria may occur between humans and their companion animals. One study investigated In fact, the prevalence of periodontal pathogen species in dogs and their owners to examine the possibility of pet-to-owner transmission has been studied. *P. gulae* was detected in 71.2% of dogs in the study and 16% in the owners. Interestingly, *P. gulae* is extremely uncommon in the human oral cavity, and each owner who harbored the bacteria had a dog that tested positive for the pathogen. Two additional species, *E. corrodens* and *T. denticola*, were found to correlate between owners and dogs indicating that oral bacteria species may be transmitted between dogs and their owners.

The *P. gulae* bacterium, a member of the *Porphyromonas* genus found in the oral cavity of dogs, has been shown to share 60% homology with *P. gingivalis*. This suggests that *P. gulae* would respond similarly to treatment with the device as does *P. gingivalis*. Recommended treatments using systems and/or methods according to the present invention to remedy and/or prevent the transfer of oral bacteria between animals of different species by reducing or controlling such types of bacteria, may include a predetermined time, such as 20 minutes, of oral tissue exposure to an electrical current (alternating or direct current, constant or pulsed) level of between about 50 microamps (μA) and about 500 microamps (μA). Either or both animals (e.g. a dog and/or its owner) may be so treated. Devices according to the present invention have been shown to be effective at reducing the count of such bacterial species in this current range. Such treatment should reduce levels of *P. gulae* and diminish the possibility of pathogen transmission to the animal's owner.

The treatment times may be a constant treatment time (e.g. 20 consecutive minutes) or treatments may be prescribed and/or delivered for a predetermined period of time (e.g. 1-60 minutes) within a treatment window (e.g. 24 hours, one week, one month, etc.) in shorter incremental treatments, such as two minutes, five times a day (to achieve 10 minutes of stimulation within a treatment window of 24 hours).

Method of Manufacture

A mouthpiece according to the present invention may be formed using any method and means known in the art. In one embodiment of such a method, a first mold 700 is provided. The first mold 700 preferably includes a top portion 710 and a bottom portion 720. Each portion of the first mold 700 includes a sealing means for sealing the first mold 700. In the illustrated embodiment the sealing means take the form of a cap 730A,730B. Each cap 730A,730B preferably has a first channel 740 and a second channel 750 therethrough. The first mold 700 preferably includes one or more fill ports 760 and one or more vents 770.

Figure 8:
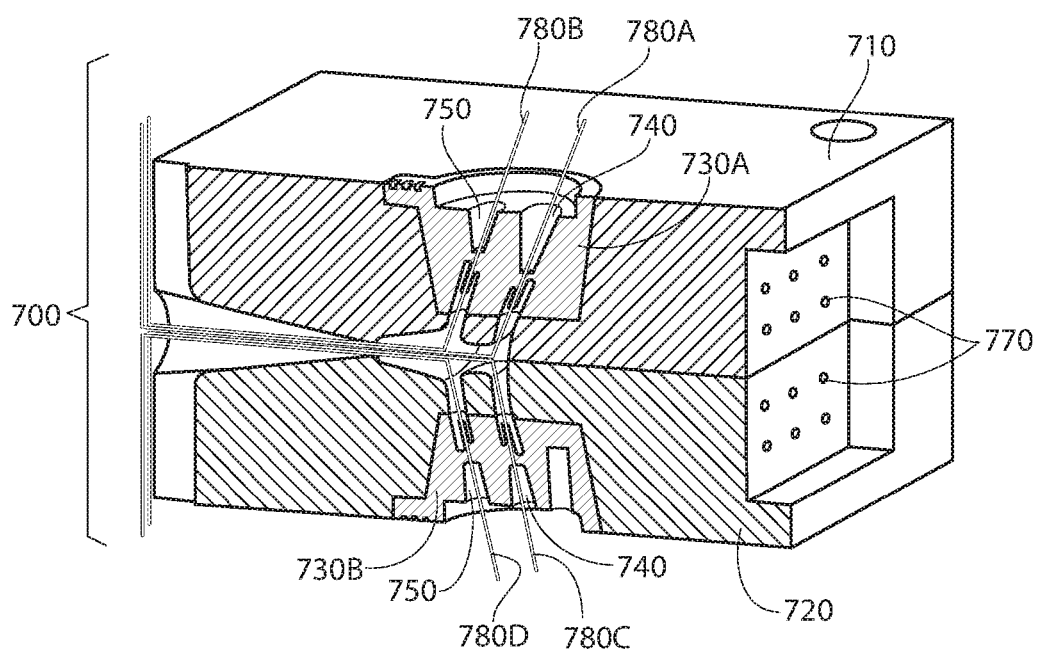
FIG. 8 is a cross sectional view of a first mold for molding a mouthpiece according to the present invention.
Figure 9:
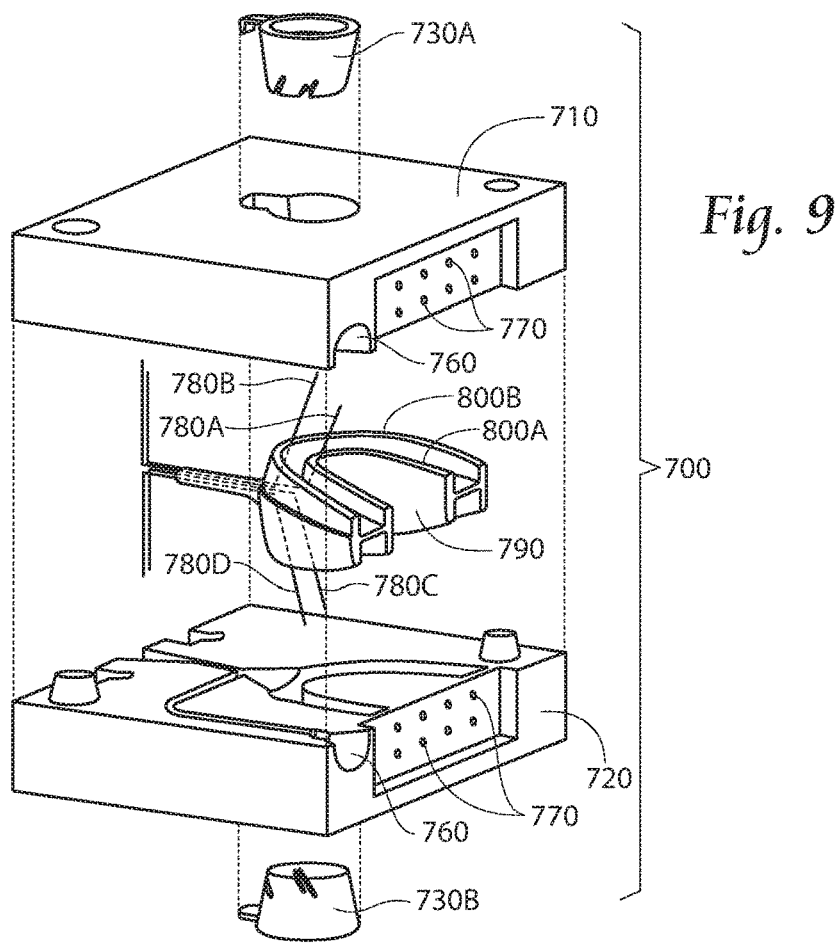
FIG. 9 is an exploded view of a first mold for molding a mouthpiece according to the present invention with a partially molded mouthpiece.
Figure 10:
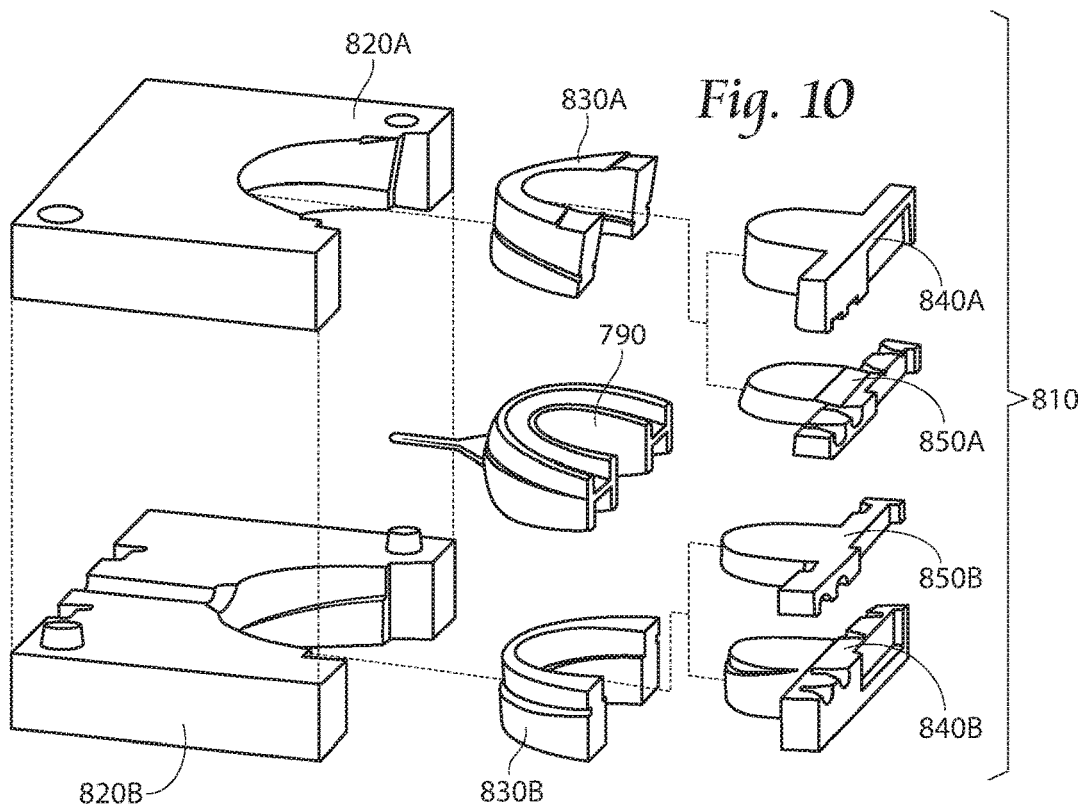
FIG. 10 is an exploded view of a second mold for molding a mouthpiece according to the present invention with a partially molded mouthpiece.
Figure 11:
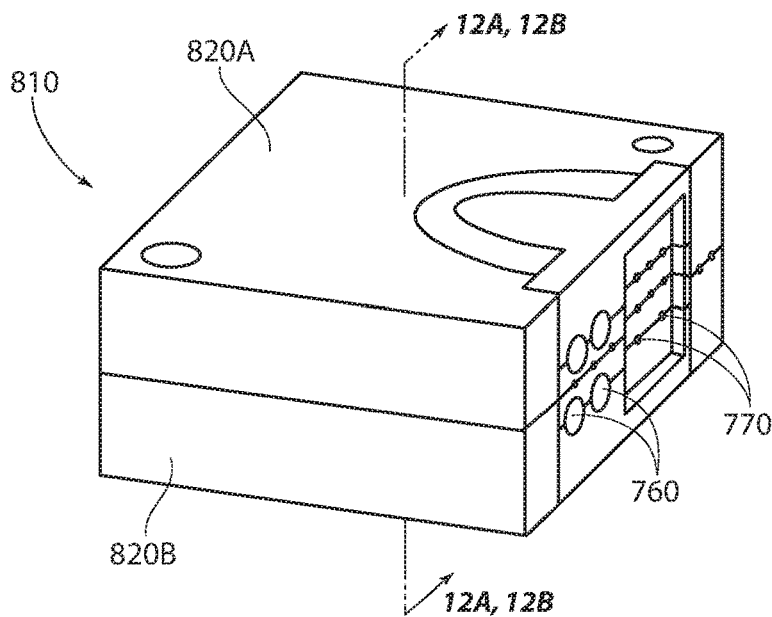
FIG. 11 is perspective view of a second mold for molding a mouthpiece according to the present invention with a partially molded mouthpiece.
Figure 12A:
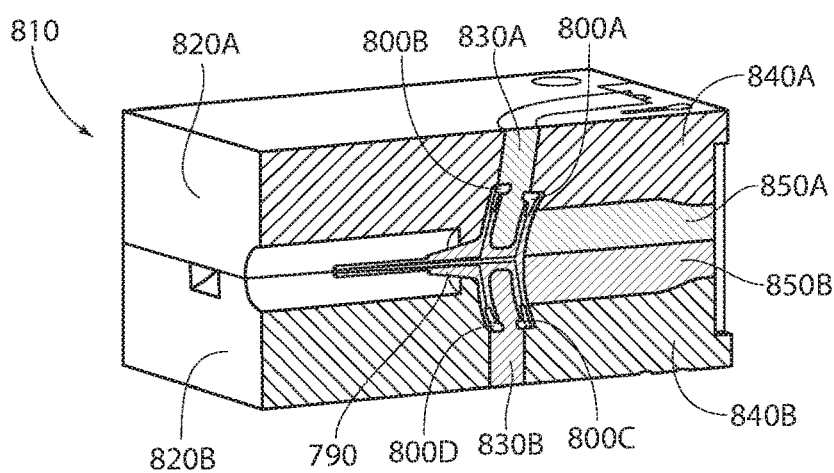
FIG. 12A is a cross section of the mold of FIG. 11 with a partially molded mouthpiece in its unfilled state.
Figure 12B:
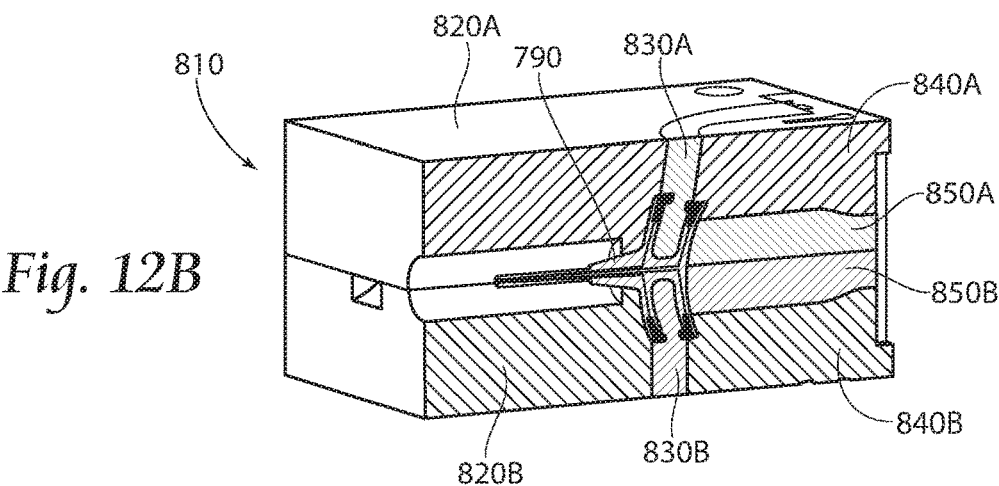
FIG. 12B is a cross section of the mold of FIG. 11 with a partially molded mouthpiece in its filled state.
Figure 13:
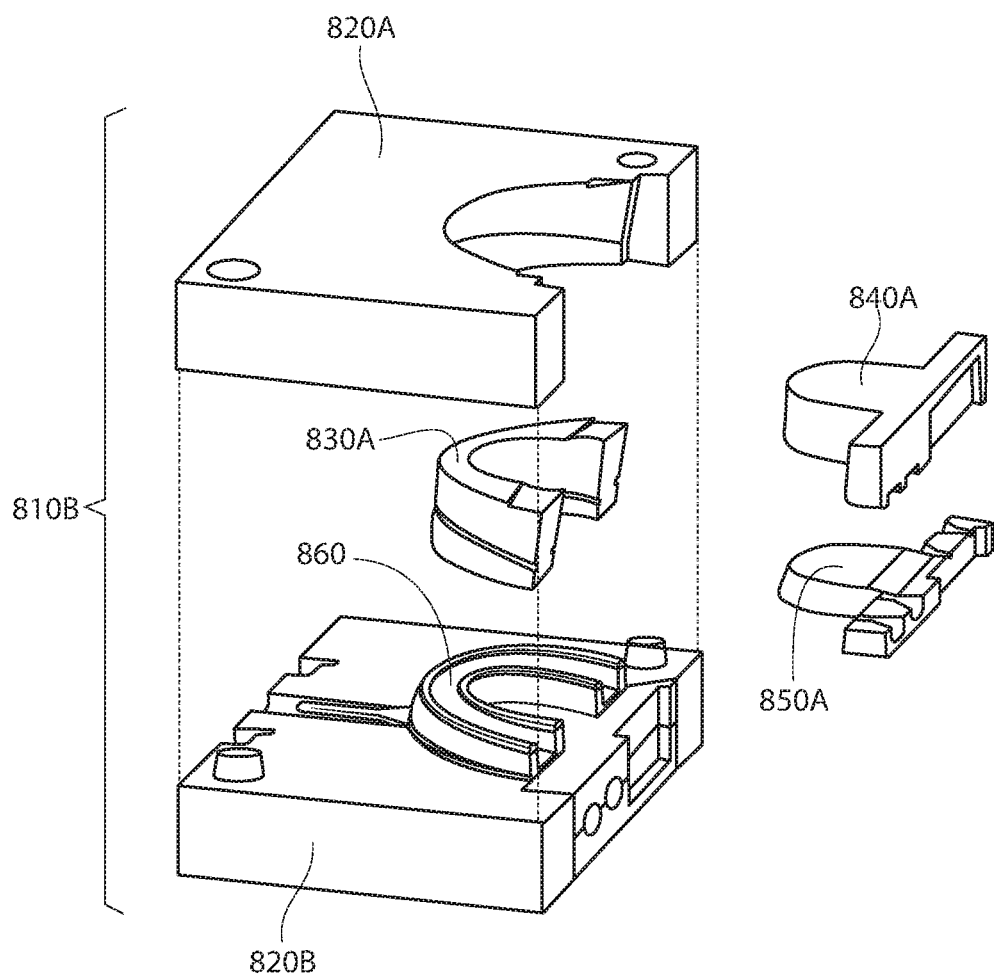
FIG. 13 is a perspective view of a mouthpiece molded according to an embodiment of the present invention.
Figure 14:
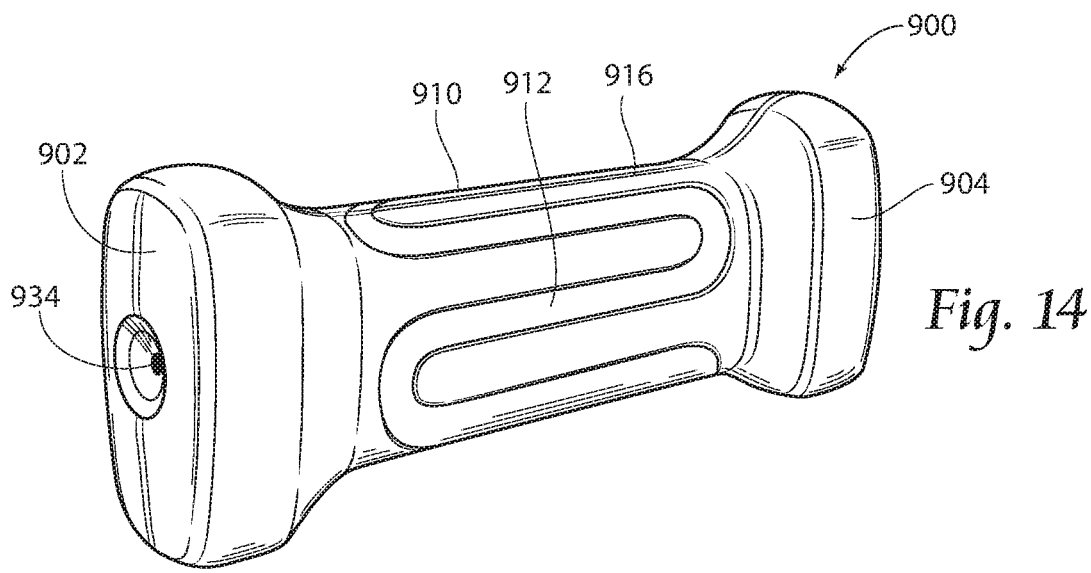
FIG. 14 is a perspective view of another embodiment of a device according to the present invention with an enclosed power supply.
Figure 15:
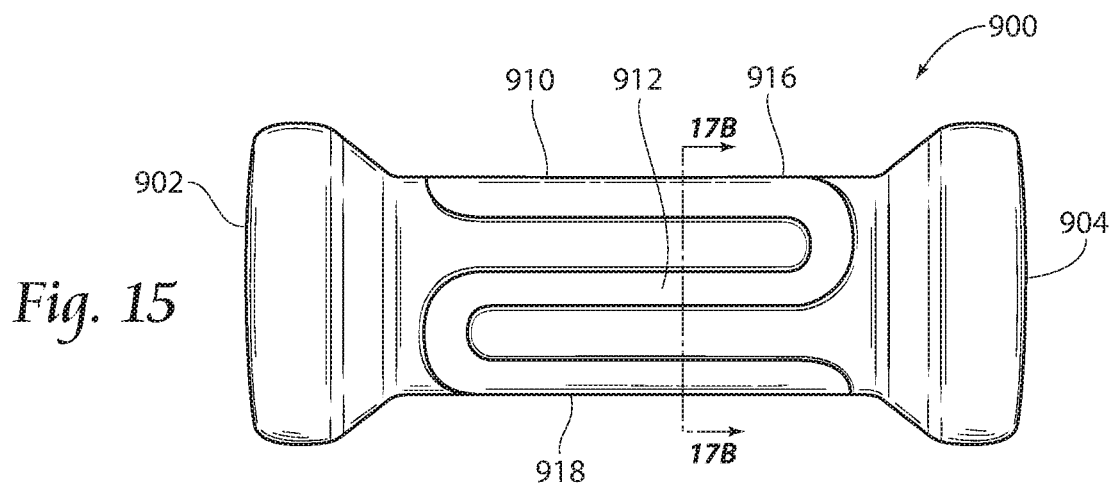
FIG. 15 is a side view of the embodiment shown in FIG. 14.
Figure 16:
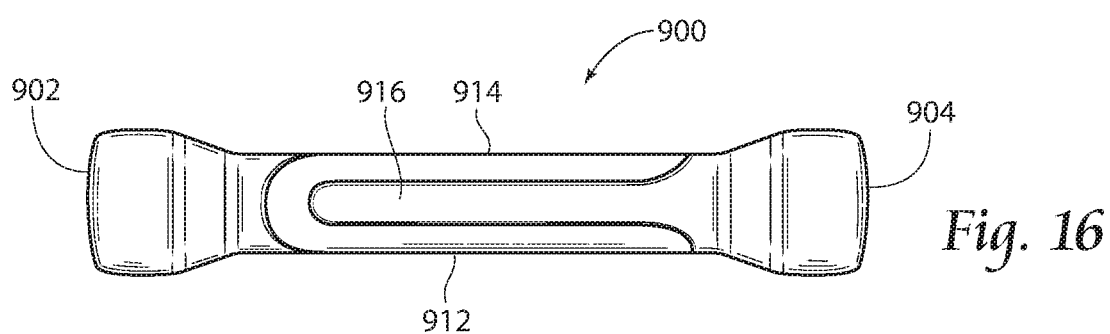
FIG. 16 is a top view of the embodiment shown in FIG. 14.

The pieces of the first mold 700 are preferably cleaned. A plurality of wires 780A,780B,780C,780D are then prepared and treaded through the first mold 700. In the preferred embodiment, the four wires 780A,780B,780C,780D are threaded through the first mold 700 as shown in FIG. 8. Preferably a first and a second wire 780A,780B are threaded through the top cap 730A and through the first mold 700 and a third and a fourth wire 780C,780D are threaded through the bottom cap 730B and through the first mold 700. Preferably the first wire 780A extends through the first channel 740 in the top cap 730A and the second wire 780B extends through the second channel 750 in the top cap 730A. Similarly, preferably, the third wire 780C extends through the first channel 740 in the bottom cap 730B and the fourth wire 780D extends through the second channel 750 in the bottom cap 730B. The first mold 700 is then closed. A non-conductive material is then injected through one or more fill ports 760 in the first mold 700. The first mold 700 cavity is filled when material is coming out of all vents 770 in the first mold 700. The non-conductive material may be a thermoplastic, a thermoplastic elastomer, a thermoset polymer, a room temperature vulcanizing elastomer, or other polymer.

When the non-conductive material is cured, the first mold 700 is preferably opened and the partially formed mouthpiece 790 is removed from the first mold 700. The plurality of wires 780A,780B, 780C,780D are now encapsulated by the non-conductive material. Preferably a wire 780A,780B, 780C,780D is located in each of the four exposed channels 800 of the mouthpiece 790. Preferably the first wire 780A is located in the inner upper channel 800A, the second wire 780B is located in the outer upper channel 800B, the third wire 780C is located in the inner lower channel 800C (not shown), and the fourth wire 780D is located in the outer lower channel 800D (not shown). The excess wire is then preferably trimmed from the mouthpiece 790 and the remaining wire 780A,780B,780C,780D is preferably inserted fully into its associated channel 800A,800B,800C, 800D.

A second mold 810 is preferably provided. The second mold preferably includes a top portion 810A and a bottom portion 810B. In the illustrated embodiment, each of the top and bottom portions of the second mold 810 preferably includes a mold base 820A,820B, a center piece 830A,830B, a first insert 840A,840B, and a second insert 850A,850B. The pieces of the second mold 850 are preferably designed to allow the channels 800A,800B,800C,800D of the mouthpiece 790 to be filled with an electrically-conductive material. The second mold 810 preferably includes one or more fill ports 760 for filling the mold cavities. As there are four channels 800A,800B,800C,800D to be filled, the preferred embodiment includes four fill ports 760. Further, the second mold 810 preferably includes one or more vents 770. In the illustrated embodiment each cavity includes its own vent 770.

Preferably the pieces of the second mold 810 are cleaned and prepared. The second mold 810 is then assembled with the mouth piece 790 as shown in FIGS. 10-12B. Preferably, the bottom portion 810B of the second mold 810 is assembled first, with the mouthpiece 790. The top portion 810A of the second mold 810 is then assembled. A conductive material is then inserted into each of the fill ports 760. The cavities are filled when material is coming out of all vents 770 in the second mold 810. The conductive material is preferably a thermosetting elastomer, but may also be a thermoplastic, a thermoplastic elastomer, or other polymer.

After the conductive material is cured, the second mold 810 is opened and the finished mouthpiece 760 is removed. Preferably, the top half 810A of the second mold 810 is removed first. The first 840A and second inserts 850A are preferably removed first. The center piece 830A can then be removed. The bottom half 810B of the second mold may then be removed, again first removing the first 840B and second inserts 850B and then the center piece 830B.

Another embodiment 900 of a treatment apparatus is shown in FIGS. 14-17B. The treatment apparatus 900 comprises a first end 902, a second end 904 opposite the first end 902, and a body 910 extending between and including the first end 902 and the second end 904.

While the ends 902,904 may be formed integrally with the body 910, at least one of the first end 902 and the second end 904 may be separable from the body 910. The combination of the first end 902, the second end 904, and the body 910 defines a cavity 920. A control board 930 with power supply 932 is preferably configured to be positioned within the cavity 920 as shown in FIG. 17A.

Figure 17A:
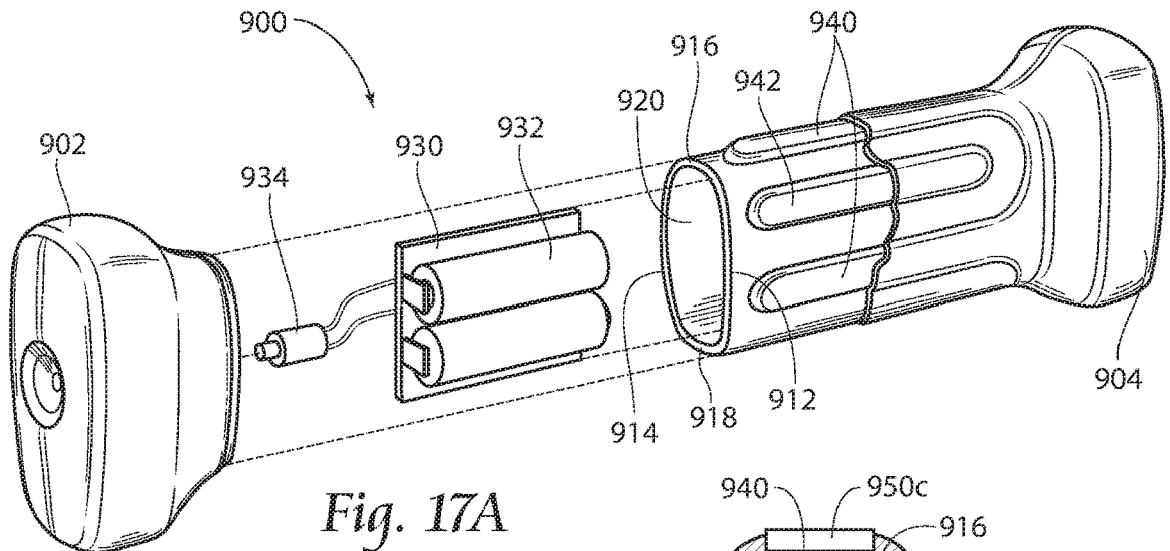
FIG. 17A is a partially-exploded perspective view of the embodiment shown in FIG. 14.
Figure 17B:
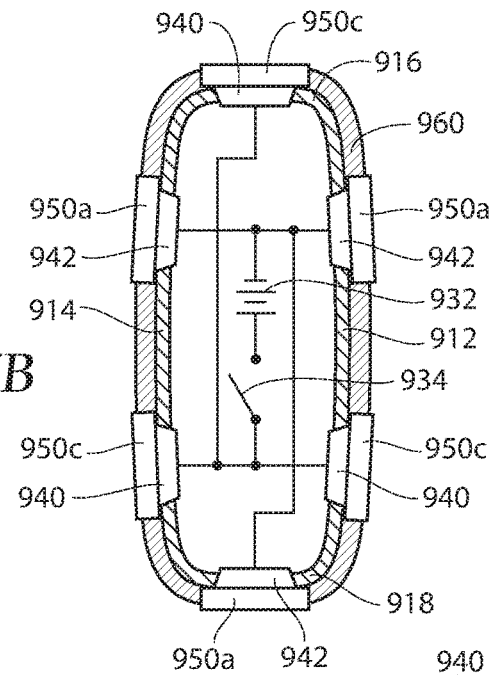
FIG. 17B is a partial schematic cross-section taken along line 17B-17B of FIG. 15.

As further shown in FIGS. 17A and 17B, at least one and preferably a plurality of cathodic electrodes 940 and at least one and preferably a plurality of anodic electrodes 942 are spaced about the body 910. The electrodes 940,942 may be spaced in an alternating fashion or in pairs. As shown here, the electrodes 940,942 extend substantially longitudinally along the body 910 and alternate cathodic electrode 940/anodic electrode 942 about the body periphery. In the embodiment 900, the body 910 has an oval-type cross-section providing a first long side 912 and an opposing second long side 914, and a first short side 916 adjacent to the first long side 912 and the second long side 914, and a second short side 918 opposing the first short side 916. At least two electrodes, one cathode and one anode, are provided and electrically accessible through the material forming the outer surface of the device. On the first long side 912, a cathodic electrode 940 and an anodic electrode 942 may be placed adjacent to, but spaced from, one another. An alternating pattern of cathodic electrodes and anodic electrodes may provide a cathodic electrode 940 or an anodic electrode 942 on the first short side 916 depending on the placement of the electrodes 940 and 942 on the first long side 912. This pattern may be continued on the second long side 914 and the second short side 918. One alternating relationship is further shown in schematic form in FIG. 18. It should be noted that alternative shapes and configurations that maintain a spaced cathodic electrode 940 and anodic electrode 942 configuration are within the scope of the present invention.

Figure 18:
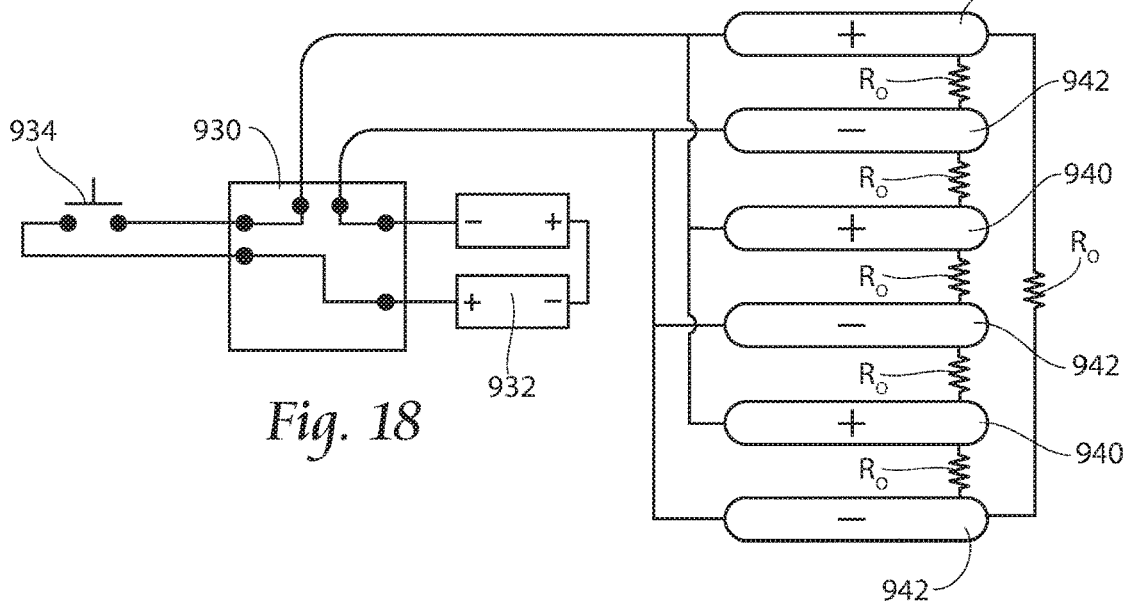
FIG. 18 is a schematic illustrating an electrode arrangement according to the present invention.

As discussed previously, the circuit will be completed by the animal's mouth. This is schematically represented in FIG. 18 by impedances $R_o$, provided by the animal's mouth (e.g. saliva and/or oral tissues), extending between two or more electrodes. An alternating pattern of a plurality of cathodic electrodes 940 and a plurality of anodic electrodes 942 may provide a higher likelihood of circuit completion, as there is provided more opportunities therefore. As one of each type of electrode 940 and 942 come into contact with an animal's mouth or oral tissues or secretions, an electrical current flows from the contacted cathodic electrodes 940 to the saliva, gingival tissues, surrounding teeth, boney structures, and/or connected mouth tissues ($R_o$) to the contacted anodic electrodes 942 and then back to a power supply 932, forming a complete circuit. The power supply 932 may be a simple dry-cell battery, a rechargeable battery, a capacitor, a kinetic energy generator, a piezoelectric generator, a microcontrolled DC power supply (as previously discussed 110) or other power supply (such as a microcontrolled AC power supply). Regardless of the power supply 932 used, it is most preferable to control the amount of electrical current delivered by the treatment device to provide a relatively constant current power source to provide up to about 500 microamps of direct or alternating current. Such control may be provided by a microcontroller or discrete monitoring circuitry (such as through current and/or impedance sensing), or optimal dry-cell design if expected impedances are generally known. It is further contemplated by the present invention that the treatment apparatus 900 is preferably used by non-human animals, such as felines, bovines, ovines, canines, equines, porcines, etc.

Furthermore, a conductive material 950$c,a$ is layered over the top of the electrodes 940,942, respectively. Preferably, the conductive material 950 comprises a resilient material (preferably durometer Shore A range of about 25 to about 80, or even up to about 90-95) to encourage chewing of the treatment apparatus 900. As non-limiting examples, a conductive silicone, urethane, fluorosilicone, or other conductive polymer or a conductive fabric (e.g. silver-plated nylon, or non-woven conductive or conductive-through-adhesive fabric tape) may be used as, or as a part of, the covering material. Regardless of the covering material used, it is preferred that at least a portion of the material forming the outer surface of the apparatus conducts electricity from the power supply, or regulated amount thereof, to the animal's mouth. The conductive material portions 950 are preferably separated by non-conductive material 960, such as an insulative polymer (e.g. non-conductive silicone) or fabric, preferably having approximately the same durometer Shore A hardness as the conductive material, or a similar tooth feel thereto. Alternatively, in another preferred embodiment, the hardness of the non-conductive material 960 is less than that of the conductive material 950, such as about half.

The control board 930 and power supply 932 may be of any types known to provide an ability to transfer the power of the power supply 932 to the electrodes 940 and 942. Fully contemplated within the purview of the present invention are timers, audible and/or visible usage, activity and/or power indicators (e.g. beeper, buzzer, light-emitting diodes), motion activation, moisture activation, pressure activation, electrical current intensity adjustment (e.g., based on sensed impedance between a cathode 940 and an anode 942), and/or an on/off switch 934 to control the possible current delivery by the power supply 932. Optionally, a microcontroller could be used, as previously described, to control the various functions and could record various treatment parameters and/or treatment history in non-volatile memory to be analyzed in real-time or post-treatment.

Further contemplated is the use of a method according to the present invention for promoting oral hygiene in non-human animals, such as felines, bovines, ovines, canines, porcines, and/or equines. The method comprises the steps of providing a treatment apparatus comprising a power source and a plurality of electrodes electrically coupled to the power source. The power source may be an internal direct current power source, or other power source as described above. The plurality of electrodes includes at least one, but preferably a plurality of cathodic electrodes and at least one, but preferably a plurality of anodic electrodes. The electrodes may be positioned in a spaced arrangement about, and preferably conductive through, the exterior of the treatment apparatus by a conductive material. The electrodes may be arranged in an alternating cathodic/anodic fashion about the device. The method further comprises the step of providing such device to a non-human animal, thereby allowing delivery of electrical current from the power source, through the electrodes and to at least one of the animal's oral secretions (e.g., saliva) and oral tissue (e.g., lingual tissue, dental tissue, gingival tissue, periodontal tissue, and oral mucosa tissue).

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An apparatus for promoting oral hygiene in a non-human animal comprising:
   a body sized and configured to be received in the non-human animal mouth, the body extending along a longitudinal length between and including a first end and an opposite second end and defining a cavity therewithin;
   a plurality of cathodic electrodes supported by the body;
   a plurality of anodic electrodes supported by the body spaced from the plurality of cathodic electrodes;
   wherein the plurality of cathodic electrodes and the plurality of anodic electrodes are disposed in alternating fashion circumferentially about the body; and
   a power supply housed within the cavity and being electrically connected to the plurality of cathodic electrodes and the plurality of anodic electrodes.

2. The apparatus of claim 1 further comprising a first conductive material portion secured over the plurality of cathodic electrodes.

3. The apparatus of claim 2 further comprising a second conductive material portion secured over the plurality of anodic electrodes.

4. The apparatus of claim 3 further comprising an insulative portion disposed at least partially between the first conductive material portion and the second conductive material portion.

5. The apparatus of claim 1, wherein the plurality of cathodic electrodes and the plurality of anodic electrodes are centered along the longitudinal length of the body between the first end and the second end.

6. The apparatus according to claim 1, wherein the body has a substantially geometric stadium cross-section at its longitudinal mid-point, the cross-section having two opposite substantially straight sides connected by two opposite substantially curved ends.

7. The apparatus according to claim 6, wherein the plurality of cathodic electrodes further comprises a third cathodic electrode, wherein the plurality of anodic electrodes further comprises a third anodic electrode, wherein each straight side comprises one of the plurality of cathodic electrodes and one of the plurality of anodic electrodes, and wherein one of the two curved ends comprises one of the plurality of cathodic electrodes and the other of the two curved ends comprises one of the plurality of anodic electrodes.

8. The apparatus of claim 4, wherein the conductive material portions extend radially outward beyond the insulative portion.

9. The apparatus of claim 8, wherein the conductive material portions comprise a resilient material having a hardness value on the Shore A durometer hardness scale.

10. The apparatus of claim 9, wherein the conductive material portions have a Shore A hardness value of 25-80 on the Shore A durometer hardness scale.

11. The apparatus of claim 4, wherein the insulative portion comprises a resilient material of approximately the same hardness as the conductive material portion.

12. The apparatus of claim 4, wherein the insulative portion comprises a resilient material having a hardness approximately half the hardness of the conductive material portions.

13. An apparatus for promoting oral hygiene in a non-human animal comprising:
a body sized and configured to be received in the non-human animal mouth, the body extending along a longitudinal length between and including a first end and an opposite second end and defining a cavity therewithin;
a cathodic electrode supported by the body;
a anodic electrode supported by the body;
a power supply housed within the cavity and being electrically connected to the cathodic electrode and the anodic electrode: and
a control board, comprising a timer, housed within the cavity configured to facilitate the transfer of the power of the power supply to the cathodic electrode and the anodic electrode, wherein the timer is configured to deactivate the electrodes at a predetermined time after activation.

14. The apparatus of claim 13 further comprising a first conductive material portion secured over the cathodic electrode.

15. The apparatus of claim 14 further comprising a second conductive material portion secured over the anodic electrode.

16. The apparatus of claim 15 further comprising an insulative portion disposed at least partially between the first conductive material portion and the second conductive material portion.

* * * * *